(12) United States Patent
Han et al.

(10) Patent No.: US 11,300,574 B2
(45) Date of Patent: Apr. 12, 2022

(54) METHODS FOR TREATING BREAST CANCER AND FOR IDENTIFYING BREAST CANCER ANTIGENS

(71) Applicant: UNIVERSITY OF CONNECTICUT, Farmington, CT (US)

(72) Inventors: David Han, Farmington, CT (US); Veneta Qendro, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 827 days.

(21) Appl. No.: 15/990,172

(22) Filed: May 25, 2018

(65) Prior Publication Data

US 2018/0340944 A1    Nov. 29, 2018

Related U.S. Application Data

(60) Provisional application No. 62/511,767, filed on May 26, 2017.

(51) Int. Cl.

| | |
|---|---|
| *G01N 33/68* | (2006.01) |
| *C07K 14/47* | (2006.01) |
| *G01N 33/574* | (2006.01) |
| *C07K 4/00* | (2006.01) |
| *C07K 4/12* | (2006.01) |
| *C07K 17/00* | (2006.01) |
| *C07K 1/13* | (2006.01) |
| *C07K 17/02* | (2006.01) |
| *C07K 17/14* | (2006.01) |

(52) U.S. Cl.
CPC ........... *G01N 33/6878* (2013.01); *C07K 4/00* (2013.01); *C07K 4/12* (2013.01); *C07K 14/4748* (2013.01); *C07K 17/00* (2013.01); *G01N 33/57415* (2013.01); *G01N 33/57488* (2013.01); *G01N 33/6845* (2013.01); *C07K 1/13* (2013.01); *C07K 17/02* (2013.01); *C07K 17/14* (2013.01); *G01N 2800/52* (2013.01)

(58) Field of Classification Search
CPC ... C07K 1/13; C07K 4/00; C07K 4/12; C07K 14/4748; C07K 17/00; C07K 17/02; C07K 17/14; G01N 33/57415; G01N 33/57488; G01N 33/6845; G01N 33/6878; G01N 2800/52
See application file for complete search history.

(56) References Cited

PUBLICATIONS

UniProtKB P52179 (Year: 2008).*
UniProtKB Q685J3 (Year: 2010).*
Beal M. A.,Glenn, T. C., Somers, C. M., Whole genome sequencing for quantifying germline mutation frequency in humans and model species: cautious optimism. Mutat. Res. 2012, 750, 96-106.
Beyer, M., Nesterov A., Block, I., Konig, K., et al., Combinatorial synthesis of peptide arrays onto a microchip. Science 2007,318, 1888.
Biankin A. V., Waddell, N., Kassahn, K. S., Gingras M. C., et al., Pancreatic cancer genomes reveal aberrations in axon guidance pathway genes. Nature 2012,491, 399-405.
Chalmers, Z. R., Connelly, C. F., Fabrizio, D., Gay, L., et al. Analysis of 100,000 human cancer genomes reveals the landscape of tumor mutational burden. Genome Medicine 9:34 (2017).
Curtis, C., Shah, S. P., Chin, S. F., Turashvili, G., et al., The genomic and transcriptomic architecture of 2,000 breast tumours reveals novel subgroups. Nature 2012, 486, 346-352.
Ellis, M. J., Ding, L., Shen, D., Luo, J., et al., Whole-genome analysis informs breast cancer response to aromatase inhibition. Nature 2012, 486, 353-360.
Erdag, G., Schaefer, J. T., Smolkin, M. E., Deacon, D. H., et al., Immunotype and immunohistologic characteristics of tumor-infiltrating immune cells are associated with clinical outcome in metastatic melanoma. Cancer Res. 2012, 72, 1070-1080.
Forbes, S. A. et al. COSMIC: mining complete cancer genomes in the Catalogue of Somatic Mutations in Cancer. Nucl. Acids Res. 39 (suppl 1), D945-D950 (2011).
Frankel, J. C., Immune therapy steps up the attack. Science 2010, 330, 440-443.
Frankel, J. C., The dizzying journey to a new cancer arsenal. Science 2013, 340, 1514-1518.
Gundry, M., Vijg, J., Direct mutation analysis by high-throughput sequencing: from germline to low-abundant, somatic variants. Mutat. Res. 2012, 729, 1-15.
Jiang, Q., Crews, L. A., Holm, F., Jamieson, C. H. M. RNA editing-dependent epitranscriptome diversity in cancer stem cells. Nature Reviews Cancer (2017) doi:10.1038/nrc.2017.23.
Jones, S., Zhang, X., Parsons, W. D., Lin, J. Ch., et al. Core signaling pathways in human pancreatic cancers revealed by global genomic analyses. Science 2008, 321, 1801-1806.
June, C., Rosenberg, S. A., Sadelain, M., Weber, J. S., et al., T-cell therapy at the threshold.Nat. Biotechnol. 2012, 30, 611-4.
Larimore, K., Mccormick. M. W., Robins, H., Greenberg, P., Shaping of Human Germline IgH Repertoires Revealed by Deep Sequencing. J. Immunology 2012, 189, 3221-3230.
Le, D.T., Uram, J. N., Wang, H., Bartlett, B. R., et al. PD-1 Blockade in tumors with mismatch-repair deficiency. N Engl J Med. 372:2509-20 (2015).

(Continued)

*Primary Examiner* — Jeremy C Flinders
(74) *Attorney, Agent, or Firm* — McDonnell Boehnen Hulbert & Berghoff LLP

(57) ABSTRACT

Disclosed herein are isolated compositions including at least 2 of mutant peptides selected from the group consisting of SEQ ID NOS: 1-149, or polypeptides comprising the mutant peptides; wherein the composition comprises mutant peptides encoded by 2 or more genes. Also disclosed are methods for personalized treatment of breast cancer involving creating a peptide array of mutant peptides comprising the mutations in protein-encoding regions of the high-frequency cancer genes or the exome in a subject and screening the peptide array with a biological sample from the subject to detect antibodies in the biological sample that bind to the array, to detect antigenic targets for therapy in treating the subject.

6 Claims, No Drawings

Specification includes a Sequence Listing.

(56) References Cited

PUBLICATIONS

Leach, D. R., Krummel, M. F., Allison, J. P. Enhancement of antitumor immunity by CTLA-4 blockade. Science 1996, 271, 1734-1736.
Lee, H. J., Kim, J. Y., Park, I. A., Song, I. H., et al. Prognostic Significance of Tumor-Infiltrating Lymphocytes and the Tertiary Lymphoid Structures in HER2-Positive Breast Cancer Treated With Adjuvant Trastuzumab. Am. J. Clin. Pathol. 2015, 144, 278-288.
Linnebacher, M.,Tumor-infiltrating B cells come into vogue. World J Gastroenterol 2013, 19, 8-11.
Martincorena, I., Roshan, A., Gerstung, M., Ellis, P., et al. High burden and pervasive positive selection of somatic mutations in normal human skin. Science 2015, 348, 880-886.
Mertes, F., Elsharawy, A., Sauer, S., van Helvoort, J. M, et al., Targeted enrichment of genomic DNA regions for next-generation sequencing. Genomics 2011, 10, 374.
Mertins, P., Mani, D. R., Ruggles, K. V., Gillette, M. A., et al. Proteogenomics connects somatic mutations to signalling in breast cancer. Nature 534, 55-62 (Jun. 2, 2016) doi:10.1038/nature18003.
Nelson, B. H., CD20+ B cells: the other tumor-infiltrating lymphocytes. J. Immunol. 2010, 185, 4977-4982.
Nielsen J. S., Sahota, R. A., Milne, K., Kost, S. E., et al. CD20+ tumor-infiltrating lymphocytes have an atypical CD27-memory phenotype and together with CD8+ T cells promote favorable prognosis in ovarian cancer. Clin. Cancer Res. 2012, 18, 3281-3292.
Pardoll, D. M. Immunology beats cancer: a blueprint for successful translation. Nat. Immunol. 2012, 13, 1129-1132.
Parson, D.W., Jones, S., Zhang, X., Lin,J. Ch., et al., An integrated genomic analysis of human glioblastoma multiforme. Science 2008, 321, 1807-1812.
Pavelka, N., Pelizzola, M., Vizzardelli, C., Capozzoli., et al., A power law global error model for the identification of differentially expressed genes in microarray data. BMC Bioinformatics 2004,5, 203-214.
Qendro, V., Bugos, G.A., Lundgren, D. H., Glynn, J., et al. Integrative proteomics, genomics, and translational immunology approaches reveal mutated forms of Proteolipid Protein 1 (PLP1) and mutant-specific immune response in multiple sclerosis. Proteomics. Mar. 2017;17(6). doi: 10.1002/pmic.201600322.
Rizvi, N. A., Hellmann, M.D., Snyder, A., Kvistborg, P., et al. Cancer immunology. Mutational landscape determines sensitivity to PD-1 blockade in non-small cell lung cancer. Science. 2015, 348:124-8.
Robins, H. S., Campregher, P. V., Srivastava, S. K., Wacher, A., et al. Comprehensive assessment of T-cell receptor beta-chain diversity in alphabeta T cells. Blood 2009,114: 4099-4107.
Rosenberg, S. A., Restifo, N. P., Adoptive cell transfer as personalized immunotherapy for human cancer. Science 2015, 348, 62-8.
Rosenberg, S. A., Yang, J. C. & Restifo, N. P. Cancer immunotherapy: moving beyond current vaccines. Nat. Med. 10, 909-915 (2004).
Schmidt, M., Böhm, D., von Törne, C., Steiner, E., et al., The humoral immune system has a key prognostic impact in node-negative breast cancer. Cancer Res. 2008, 68, 5405-5413.
Schumacher, T. et al. A vaccine targeting mutant IDH1 induces antitumour immunity. Nature 512, 324-327 (2014).
Sjöblom, T., Jones, S., Wood, L. D., Parsons W. D., et al., The consensus coding sequences of human breast and colorectal cancers. Science 2006, 314, 268-274.
Snyder, A., Makarov, V., Merghoub, T., Yuan, J., et al. Genetic basis for clinical response to CTLA-4 blockade in melanoma. N Engl J Med. 2014; 371:2189-99.
Takahashi, K., Tanabe, K., Ohnuki, M., Narita, Megumi., et al., Induction of pluripotent stem cells from adult human fibroblasts by defined factors. Cell 2007, 131, 861-872.
The Cancer Genome Atlas Network. Comprehensive molecular portraits of human breast tumours. Nature 2012, 490, 61-70.
Topalian, S. L., Hodi, S. F., Brahmer, J. R., Gettinger, S. N., et al., Safety, activity, and immune correlates of anti-PD-1 antibody in cancer. N. Engl. J. Med. 2012, 366, 2443-2454.
Tran, E. et al. Cancer immunotherapy based on mutation-specific CD4+ T cells in a patient with epithelial cancer. Science 344, 641-645 (2014).
Van Rooij, N., van Buuren, M. M., Philips, D., Velds, A., et al. Tumor exome analysis reveals neoantigen-specific T-cell reactivity in an ipilimumab-responsive melanoma. J. Clin. Oncol. 2013, 31, 439-42.
Vogelstein, B., Papadopoulos, N., Velculescu, V. E., Zhou, Sh., et al., Cancer genome landscapes. Science 2013, 339, 1546-1558.
Wolchok, J. D., Kluger, H., Callahan, M. K., Postow, M. A., et al., Nivolumab plus ipilimumab in advanced melanoma. N. Engl. J. Med. 2013, 369, 122-133.
Yu, J., Vodyanik, M. A., Smuga-Otto, K., Antosiewicz-Bourget, J., et al., Induced pluripotent stem cell lines derived from human somatic cells. Science 2007, 318, 1917-1920.

* cited by examiner

METHODS FOR TREATING BREAST CANCER AND FOR IDENTIFYING BREAST CANCER ANTIGENS

CROSS REFERENCE

This application claims priority to U.S. Provisional Patent Application Ser. No. 62/511,767 filed May 26, 2017, incorporated by reference herein in its entirety.

BACKGROUND

Recent advances in cancer immuno-therapeutics such as checkpoint inhibitors, chimeric antigen-receptor T cells, and tumor infiltrating T cells (TIL) are now significantly impacting cancer patients in a positive manner. Although very promising, reports indicate no more than 25% of cases result in complete remission. One of the limitations of these treatments is the identity of putative cancer antigens in each patient as it is technically challenging to identify of cancer antigens in a rapid fashion. Thus, identification of cancer antigens followed by targeted treatment will increase the efficacy of cancer immunotherapies.

SUMMARY

In one aspect the disclosure provides isolated compositions comprising at least 2 of the mutant peptides selected from the group consisting of SEQ ID NOS: 1-149, or polypeptides comprising the mutant peptides; wherein the composition comprises mutant peptides encoded by 2 or more genes. In one embodiment, the composition further comprises one or more wild type peptides corresponding to the mutant peptides, or polypeptides comprising the wild type peptides. In another embodiment, the total number of mutant and wild type peptides, or polypeptides comprising the mutant and wild type peptides, is 100,000 or less. In further embodiments, the peptides may be detectably labeled, and/or the peptides may be immobilized on the surface of a solid support.

In another aspect the disclosure provides methods for personalized treatment of breast cancer, comprising:

(a) performing sequence analysis of high-frequency cancer genes, or performing whole exome sequencing on DNA from a biological sample from a subject having breast cancer;

(b) identifying mutations in protein-encoding regions of the high-frequency cancer genes or the exome;

(c) creating a peptide array of mutant peptides comprising the mutations in protein-encoding regions of the high-frequency cancer genes or the exome, and optionally comprising wild-type counterparts of the mutant peptides;

(d) contacting the peptide array with a biological sample from the subject for a time and under conditions to permit binding of antibodies in the serum to the mutant peptides and/or the wild-type counterparts thereof; and (e) detecting binding of antibodies in the serum to the mutant peptides and/or the wild-type counterparts thereof, thus identifying antigenic targets for therapy in treating the subject.

In another aspect, the disclosure provides methods for monitoring breast cancer immunotherapy, comprising (a) contacting a biological sample from a subject who is undergoing or has undergone breast cancer therapy with a peptide array prepared according to the methods of the disclosure, or with a composition of the invention; and (b) determining an amount of antibodies against the one or more peptides in the bodily fluid sample;

wherein an increase in the amount of antibodies relative to a control, such as a baseline level of antibodies in a similar bodily fluid sample from the subject indicates efficacy of the breast cancer immunotherapy in the subject; or wherein a decrease or no increase in the amount of antibodies relative to a control, such as a baseline level of antibodies in a similar bodily fluid sample from the subject indicates that the immunotherapy is ineffective in the subject.

DETAILED DESCRIPTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, $2^{nd}$ Ed.* (R. I. Freshney. 1987. Liss, Inc. New York, N.Y.), and *Gene Transfer and Expression Protocols*, pp. 109-128, ed. E. J. Murray, The Humana Press Inc., Clifton, N.J.

As used herein, the singular forms "a", "an" and "the" include plural referents unless the context clearly dictates otherwise. "And" as used herein is interchangeably used with "or" unless expressly stated otherwise.

All embodiments of any aspect of the disclosure can be used in combination, unless the context clearly dictates otherwise.

Disclosed herein in a first aspect are isolated compositions, comprising at least 2 of the peptides selected from the group consisting of SEQ ID NOS: 1-149, or polypeptides comprising the peptides; wherein the composition comprises peptides encoded by 2 or more genes. As described in the examples below, peptides comprising or consisting of the amino acid sequence of SEQ ID NOS:1-149 were identified as tumor antigens from human breast cancer (BCa) patients, with the antigens being mutant peptides arising from single nucleotide variants (SNVs), as well as insertions and deletions that results into frame-shift mutations. Thus, the compositions may be used, for example, in identifying patient-specific tumor antigens for patient-specific immunotherapeutics. In one embodiment, the compositions may be contacted with antibodies from a patient (such as a patient having BCa) to identify the tumor antigens that are generating an immune response (positive antigens) in the patient. Antibodies against such positive antigens may then be generated/administered to the patient as an immunotherapeutic.

In various embodiments, the composition comprises least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or all 149 of the peptides having the amino acid sequence of SEQ ID NO:149, or polypeptides comprising peptides having the amino acid sequence of SEQ ID NOS: 1-149.

In other embodiments, the composition comprises mutant peptides encoded by 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or all 90 genes listed in Table 1.

TABLE 1

(149 mutants; 90 genes)

| Gene | Mutation | Mutant peptide | Highest mut/wt | Sample Type |
|---|---|---|---|---|
| AADACL3 | L350P | SMRILSALVQFVKG (SEQ ID NO: 1) | 2.1 | malignant |
| ABCF1 | del4-218_218 | SVLRSSQCQPVMRRM (SEQ ID NO: 2) | 2.9 | malignant |
| ABCF1 | del7-218_218 | PAEGRKPRVVMFLQP (SEQ ID NO: 3) | 2.1 | malignant |
| ADAM12 | G479E | DCQLKPA TACRDSS (SEQ ID NO: 4) | 2.7 | malignant |
| AKAP6 | P1839T | SSSEMTN SDTLNIE (SEQ ID NO: 5) | 2.3 | malignant |
| ALPK2 | P1449S | GHEAEIC AILQVPC (SEQ ID NO: 6) | 2.2 | malignant |
| APC | del3-4260_4260 | AEVKHLHHLLKQLKP (SEQ ID NO: 7) | 2 | malignant |
| APC | del6-4731_4734 | TGCNPKSMLVLHRGM (SEQ ID NO: 8) | 2.8 | malignant |
| APC | del1-3920_3924 | DSANTLQIAERKDWN (SEQ ID NO: 9) | 2.2 | malignant |
| ATR | D564H | LDLEATI KVVKIYD (SEQ ID NO: 10) | 2.2 | malignant |
| BAIAP2L2 | del1-1322_1363 | LDRPGNSTPSRVPSR (SEQ ID NO: 11) | 2 | malignant |
| BAX | del1-114_114 | RAGRMGGRHPSWPWT (SEQ ID NO: 12) | 2.3 | malignant |
| BGN | K288N | ELHLDNN LARVPSG (SEQ ID NO: 13) | 2.6 | benign |
| BRAF | V600E | GDFGLAT KSRWSGS (SEQ ID NO: 14) | 1.8 | benign |
| BRCA1 | E1038G | IRENVFK ASSSNIN (SEQ ID NO: 15) | 2 | malignant |
| BRD3 | del2-71_71 | PTPASPAARPTSCST (SEQ ID NO: 16) | 2 | malignant |
| BRSK1 | ins3-1127_1127 | EAATRAEVHGSPEHH (SEQ ID NO: 17) | 2 | malignant |
| C04A2 | G67D | RGQPGPV PQGYNGP (SEQ ID NO: 18) | 2 | malignant |
| CALR | del2-1095_1140 | RRMMRTKMRMRRMRR (SEQ ID NO: 19) | 2.7 | malignant |
| CALR | del4-1095_1140 | RRKMSPARPRTSCRA (SEQ ID NO: 20) | 2.3 | malignant |
| CALR | del2-1092_1143 | MMRTKMRMRRMRRTR (SEQ ID NO: 21) | 2.3 | malignant |
| CALR | del3-1102_1135 | MRMRRMRRTRRKMRR (SEQ ID NO: 22) | 2.8 | malignant |
| CDC42EP1 | del1-758_778 | NPPAPAATPTGPAAN (SEQ ID NO: 23) | 2.3 | malignant |
| CDKN2A | del1-233_234 | NCADPATHPTRARRC (SEQ ID NO: 24) | 4.1 | malignant |
| CDKN2A | del187 | SARVAELTAPTPPLS (SEQ ID NO: 25) | 10.5 | malignant |
| CDKN2A | del2-233_234 | RARRCPGGLPGHAGG (SEQ ID NO: 26) | 2.3 | malignant |
| CDKN2A | del3-233_234 | GHAGGAAPGRGAAGR (SEQ ID NO: 27) | 2.7 | malignant |
| CEBPA | del5-26_26 | ASTRRPSTSAPTSTR (SEQ ID NO: 28) | 3.9 | malignant |
| CEBPA | del6-26_26 | PTSTRPPSTTSSWPT (SEQ ID NO: 29) | 2.2 | malignant |
| CEBPA | ins5-27_27 | RARDVHRHQRLHRPG (SEQ ID NO: 30) | 2.4 | malignant |
| CEBPA | ins6-27_27 | LHRPGRLQRRVPGRP (SEQ ID NO: 31) | 2 | malignant |
| CEBPA | ins8-27_27 | AAGEGQGGRGPHGRR (SEQ ID NO: 32) | 2.3 | malignant |
| CEP164 | del3-337_337 | RTETPPKVRWPWVPH (SEQ ID NO: 33) | 3 | malignant |
| CHEK2 | K373E | ITDFGHS ILGETSL (SEQ ID NO: 34) | 2.7 | malignant |

TABLE 1-continued (149 mutants; 90 genes)

| Gene | Mutation | Mutant peptide | Highest mut/wt | Sample Type |
|---|---|---|---|---|
| CLASRP | L198S | VEVDVDE$^S$NQEQVAD (SEQ ID NO: 35) | 8.5 | malignant |
| COBLL1 | del1-2720_2720 | AKPSSFFCRCRREYR (SEQ ID NO: 36) | 2.2 | malignant |
| CRIPAK | del12-295_323 | TCRCGVPACSHVPMR (SEQ ID NO: 37) | 2.2 | malignant |
| CRIPAK | del10-205_206 | HAECPPAHTCRRGVP (SEQ ID NO: 38) | 2.9 | malignant |
| CTCF | ins3-610_610 | LYRGGQRCRCVCLRF (SEQ ID NO: 39) | 2.4 | malignant |
| CTNNB1 | A43V | HSGATTT$^V$PSLSGKG (SEQ ID NO: 40) | 3.9 | malignant |
| CTNNB1 | del1-14_241 | MATQDIDGQYAMTRA (SEQ ID NO: 41) | 2.2 | malignant |
| DLEC1 | del1-5312_5314 | HNGLSLGPHMSSELT (SEQ ID NO: 42) | 2.5 | malignant |
| DPP6 | D475N | SQPNSSN$^N$NIQSITS (SEQ ID NO: 43) | 2.2 | benign |
| DTX3L | K209N | SPSMTEF$^N$PLSQQER (SEQ ID NO: 44) | 9 | malignant |
| DUOX1 | R76G | EPHLPNF$^G$DLSNTIS (SEQ ID NO: 45) | 2.5 | malignant |
| EGFR | del1-2237_2254 | KIPVAIKAPKANKEI (SEQ ID NO: 46) | 4.1 | malignant |
| EGFR | del1-2238_2252 | IPVAIKESPKANKEI (SEQ ID NO: 47) | 5.2 | malignant |
| EGFR | del1-2238_2255 | KIPVAIKDPKANKEI (SEQ ID NO: 48) | 4.9 | malignant |
| EGFR | del1-22392256 | IPVAIKEPKANKEIL (SEQ ID NO: 49) | 2.6 | malignant |
| EGFR | del1-22402257 | IPVAIKESKANKEIL (SEQ ID NO: 50) | 2.5 | malignant |
| EGFR | E709K | ALLRILK$^K$TEFKKIK (SEQ ID NO: 51) | 2 | malignant |
| EVX1 | R407T | SSVALDQREEVPLT$^T$ (SEQ ID NO: 52) | 2 | malignant |
| FAM157A | del1-210_218 | QQQQQQQLDLLFHQR (SEQ ID NO: 53) | 2 | malignant |
| GPRASP2 | D324V | KLRTNRE$^V$CFESESE (SEQ ID NO: 54) | 2.9 | malignant |
| GPS2 | Q240E | HGHFQPT$^E$TGFLQPG (SEQ ID NO: 55) | 3.6 | malignant |
| HDGFRP2 | del1-1721_1722 | EKEKAEETGRGGAGR (SEQ ID NO: 56) | 2.2 | malignant |
| HDGFRP2 | del2-1721_1722 | GGAGRGGGPPGEGGG (SEQ ID NO: 57) | 3.2 | malignant |
| HDGFRP2 | del5-1721_1722 | ITEGGERRGQGARGG (SEQ ID NO: 58) | 3.4 | malignant |
| HDGFRP2 | del6-1721_1722 | GARGGSGLGGGAKVW (SEQ ID NO: 59) | 2.1 | malignant |
| HDGFRP2 | del7-1721_1722 | RGGSGLGGGAKVWLL (SEQ ID NO: 60) | 2.1 | malignant |
| HEG1 | A193E | VGYSLEI$^E$TALTSQS (SEQ ID NO: 61) | 2.8 | malignant |
| HLA-B | ins3-207_207 | VLGPEHTDLQGPGTD (SEQ ID NO: 62) | 2.4 | malignant |
| HLA-DRB1 | del1-301_301 | KDILEQAGPRWTPTA (SEQ ID NO: 63) | 3.4 | malignant |
| HLA-DRB1 | ins1-298_2981 | QKDILEQERGPRWTP (SEQ ID NO: 64) | 5.3 | malignant |
| HOXB1 | ins1-83_83 | AYSAHSAHSAPTSFP (SEQ ID NO: 65) | 2.9 | malignant |
| IPYR | K57N | VPRWSNA$^N$MEIATKD (SEQ ID NO: 66) | 10.1 | malignant |
| JPH4 | del1-1504_1504 | AWPEEWGGQAHRQRN (SEQ ID NO: 67) | 2.1 | malignant |
| JPH4 | ins1-1505_1505 | PEEWGGARRTGRGTS (SEQ ID NO: 68) | 2.1 | malignant |
| KIF6 | A386E | TGEQRTE$^E$LTEAELL (SEQ ID NO: 69) | 2.2 | malignant |
| KRAS | A59T | LLDILDT$^T$GQEEYSA (SEQ ID NO: 70) | 1.8 | malignant |
| KRT76 | L168V | NQSLLQF$^V$NVEIDPQ (SEQ ID NO: 71) | 2.4 | malignant |

TABLE 1-continued (149 mutants; 90 genes)

| Gene | Mutation | Mutant peptide | Highest mut/wt | Sample Type |
|---|---|---|---|---|
| LCN15 | K164E | YPTLGLF<sup>E</sup>DMMVMLP (SEQ ID NO: 72) | 3.2 | malignant |
| MACF1 | S3042T | MGVLGPL<sup>T</sup>IDPNMLN (SEQ ID NO: 73) | 2.2 | malignant |
| MAGEA4 | G153D | RCFPVIF<sup>D</sup>KASESLK (SEQ ID NO: 74) | 12.9 | malignant |
| MAP3K1 | del6-2824_2825 | PFFFYPICTSWHCNR (SEQ ID NO: 75) | 2.2 | malignant |
| MEN1 | del2-249_252 | SMPASPPRSEAPSTC (SEQ ID NO: 76) | 2.4 | malignant |
| MEN1 | ins1-1562_1562 | AVSGPPREASWDCRW (SEQ ID NO: 77) | 2.1 | malignant |
| MUC17 | S1083P | YSQASSS<sup>P</sup>TTADGTS (SEQ ID NO: 78) | 4.3 | malignant |
| MUC17 | T1608A | KTQVTAS<sup>A</sup>EASSSTT (SEQ ID NO: 79) | 1.5 | benign |
| MUC17 | T1784A | STPVTTS<sup>A</sup>EATSSPT (SEQ ID NO: 80) | 2.2 | malignant |
| MUC17 | T2786A | SIPVTTS<sup>A</sup>EASSSPT (SEQ ID NO: 81) | 4.6 | malignant |
| MUC17 | T664A | NTPVTTS<sup>A</sup>EATSSST (SEQ ID NO: 82) | 2.3 | malignant |
| MUC17 | T723A | STPVTTS<sup>A</sup>EASSSPT (SEQ ID NO: 83) | 4.5 | malignant |
| MUC17 | T959A | STPVTTS<sup>A</sup>EATSSPT (SEQ ID NO: 84) | 5.3 | malignant |
| MUC17 | T664A | NTPVTTS<sup>A</sup>EATSSST (SEQ ID NO: 85) | 3.9 | malignant |
| MUC17 | T959A | STPVTTS<sup>A</sup>EATSSPT (SEQ ID NO: 86) | 3.9 | malignant |
| MUC22 | ins1-1044_1044 | MAGSETTTVSTAGSE (SEQ ID NO: 87) | 4.2 | malignant |
| MUC3A | del3-1244_1245 | GDFHNHDPIFSEYRH (SEQ ID NO: 88) | 2.5 | malignant |
| MUC3A | del6-1244_1245 | YRFPDYSNRPHINIH (SEQ ID NO: 89) | 2 | malignant |
| MUC6 | ins8-4708_4708 | HPYPCTDGHFCLHPL (SEQ ID NO: 90) | 2.2 | malignant |
| MUC6 | ins9-4708_4708 | CLHPLNANRHDSSTD (SEQ ID NO: 91) | 3.5 | malignant |
| MYOM1 | R212K | SKQSTAS<sup>K</sup>QSTASRQ (SEQ ID NO: 92) | 2.2 | benign |
| NCOR1 | K178N | ASPSKLS<sup>N</sup>EELIQSM (SEQ ID NO: 93) | 2.5 | malignant |
| NCOR2 | ins1-1529_1529 | QQQQQQPDMPRSSQE (SEQ ID NO: 94) | 3.5 | malignant |
| NCOR2 | ins1-1529_1529 | QQQQQQPDDDMPRS (SEQ ID NO: 95) | 2.2 | malignant |
| NEK3 | E477K | LEPGLDE<sup>K</sup>DTDFEEE (SEQ ID NO: 96) | 2.6 | malignant |
| NFE2L2 | E79K | AQLQLDE<sup>K</sup>TGEFLPI (SEQ ID NO: 97) | 2.3 | malignant |
| NKX28 | V89G | EKRKKRF<sup>G</sup>LFSKAQT (SEQ ID NO: 98) | 2.1 | malignant |
| NPM1 | ins1-777_777 | DQEAIQDLWSAVEEV (SEQ ID NO: 99) | 2.8 | malignant |
| NR2E3 | D196N | EDADENI<sup>N</sup>VTSNDPE (SEQ ID NO: 100) | 4.5 | malignant |
| NUP210 | G1413E | VHFHDNS<sup>E</sup>DVFHAHS (SEQ ID NO: 101) | 2.8 | malignant |
| OR52D1 | ins2-608_608 | GSAGHGTGFHSHCHF (SEQ ID NO: 102) | 3 | malignant |
| PCDH15 | P69S | IKGTAGG<sup>S</sup>DPTIELS (SEQ ID NO:103) | 3 | malignant |
| PCSK5 | T1343M | EKTCKEC<sup>M</sup>PEFFLHD (SEQ ID NO: 104) | 3 | malignant |
| PDE1B | R394P | ALMEEFF<sup>P</sup>QGDKEAE (SEQ ID NO: 105) | 3.3 | malignant |
| PIK3R1 | D560G | AAEYREI<sup>G</sup>KRMNSIK (SEQ ID NO: 106) | 2 | malignant |
| PIK3R1 | G376R | TLTLRKGRNNKLIKI (SEQ ID NO: 107) | 2.2 | malignant |

TABLE 1-continued (149 mutants; 90 genes)

| Gene | Mutation | Mutant peptide | Highest mut/wt | Sample Type |
|---|---|---|---|---|
| PLCB1 | A907P | SVLTEVEPQTIEELK (SEQ ID NO: 108) | 2 | malignant |
| PRRC2A | R1152H | PPSPAPAHFTARGGR (SEQ ID NO: 109) | 2.5 | malignant |
| PSMD1 | K310N | TSSAFVGNTPEASPE (SEQ ID NO: 110) | 2 | malignant |
| RET | G593E | LRGSIVCEHEPGEPR (SEQ ID NO: 111) | 1.7 | malignant |
| SCARF2 | ins1-2304_2304 | GPPRSAPRGCLHVGR (SEQ ID NO: 112) | 2.2 | malignant |
| SF3B1 | K666E | QARHTGIEIVQQIAI (SEQ ID NO: 113) | 1.5 | benign |
| SHROOM4 | ins1-3384_3384 | KQQQQQQQQQQKQQE (SEQ ID NO: 114) | 2.8 | malignant |
| SLC3A2 | del4-892_892 | RTRGSPLRLTLWPPR (SEQ ID NO: 115) | 2.2 | malignant |
| SLITRK1 | R266Q | DLCPLKNQVDSSLPA (SEQ ID NO: 116) | 5 | malignant |
| SMAD4 | D493H | AAAGIGVHDLRRLCI (SEQ ID NO: 117) | 3.4 | malignant |
| STX5 | Q25H | QTRQNGIHTNKPALR (SEQ ID NO: 118) | 2.5 | malignant |
| SVIL | del4-4308_4308 | CVERCPWKGICWKWP (SEQ ID NO: 119) | 2 | malignant |
| SYDE2 | K937N | ENDPGDSNYTVDLLD (SEQ ID NO: 121) | 2.5 | malignant |
| TAB2 | I466T | NTKYTFKTTVSPNKP (SEQ ID NO: 121) | 2 | malignant |
| TCERG1 | del1-2800_2800 | IEALTKKRESTLGNF (SEQ ID NO: 122) | 2.3 | malignant |
| TP53 | del1-466_466 | STPPPGTASAPWPST (SEQ ID NO: 123) | 2 | malignant |
| TP53 | del2-439_439 | HPRPAPASAPWPSTS (SEQ ID NO: 124) | 2.5 | malignant |
| TP53 | del2-526_526 | MSAAQIAMVWPLLSI (SEQ ID NO: 125) | 3.4 | malignant |
| TP53 | del2-880_880 | TSCPQGALSEHCPTT (SEQ ID NO: 126) | 3.6 | malignant |
| TP53 | del7-754_754 | SEHCPTTPAPLPSQR (SEQ ID NO: 127) | 2.2 | malignant |
| TP53 | I255F | RRPILTIFTLEDSSG (SEQ ID NO: 128) | 2.3 | benign |
| TP53 | I255N | RRPILTINTLEDSSG (SEQ ID NO: 129) | 2.8 | malignant |
| TP53 | K132E | TYSPALNEMFCQLAK (SEQ ID NO: 130) | 1.6 | malignant |
| TP53 | L252P | GMNRRPIPTIITLED (SEQ ID NO: 131) | 2.5 | malignant |
| TP53 | R196P | APPQHLIPVEGNLRV (SEQ ID NO: 132) | 1.5 | malignant |
| TP53 | R249M | CMGGMNRMPILTIIT (SEQ ID NO: 133) | 2.1 | malignant |
| TP53 | R283P | ACPGRDRPTEEENLR (SEQ ID NO: 134) | 1.6 | malignant |
| TP53 | R342P | RERFEMFPELNEALE (SEQ ID NO: 135) | 3 | malignant |
| TP53 | Y220N | RHSVVVPNEPPEVGS (SEQ ID NO: 136) | 2.2 | benign |
| TP53 | del1-598_598 | HLIRVEGICVWSIWM (SEQ ID NO: 137) | 2.1 | malignant |
| TP53 | del1-751_751 | GGMNRRPS SP SSHWK (SEQ ID NO: 138) | 2.1 | malignant |
| TP53 | del4-880_880 | SQRRNHWMENISPFR (SEQ ID NO: 139) | 2.1 | malignant |
| TP53 | del5-835_835 | APLPSQRRNHWMENI (SEQ ID NO: 140) | 2 | malignant |

TABLE 1-continued (149 mutants; 90 genes)

| Gene | Mutation | Mutant peptide | Highest mut/wt | Sample Type |
|------|----------|----------------|----------------|-------------|
| TPO | del2421 | ADGAHPPATPLRGAE (SEQ ID NO: 141) | 3 | malignant |
| WDR72 | A788D | KPSRKVD*D*SLTIDTA (SEQ ID NO: 142) | 2 | malignant |
| ZC3H18 | ins2-2101_2101 | PPQEADAKRQRQWQW (SEQ ID NO: 143) | 2.2 | malignant |
| ZC3H18 | del1-2102_2102 | RRKERPARTPPGGGR (SEQ ID NO: 144) | 2 | malignant |
| ZDHHC8 | del12-1369_1369 | SACCAPRPTHSSATQ (SEQ ID NO: 145) | 4.4 | malignant |
| ZDHHC8 | del18-1369_1369 | ATLPCRRHCPRCPAP (SEQ ID NO: 146) | 2.1 | malignant |
| ZDHHC8 | del2-1369_1369 | VAFLPPMHCPTATAA (SEQ ID NO: 147) | 2.1 | malignant |
| ZNF184 | K206E | SPEETST*E*RSIKQNS (SEQ ID NO: 148) | 2 | malignant |
| ZNF605 | S82C | FGKIFNS*C*INIVHVG (SEQ ID NO: 149) | 8.3 | malignant |

In any of these embodiments, the isolated composition may further comprise one or more wild type peptides corresponding to the mutant peptides, or polypeptides comprising the wild type peptides. These wild type peptides may, for example, serve as controls to help identify antibodies that specifically recognize the mutant peptide. In various embodiments, the composition may further comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 wild type peptide counterparts to the mutant peptides of SEQ ID NOS:1-149, or polypeptides comprising the wild type peptides.

The composition may have any number of total peptides as deemed appropriate for a given use. In one embodiment, the total number of mutant and wild type peptides, or polypeptides comprising the mutant and wild type peptides, is 100,000 or less. In various further embodiments, the total number of mutant and wild type peptides, or polypeptides comprising the mutant and wild type peptides, is 75,000, 50,000, 25,000, 10,000, 7500, 5000, 2500, 1500, 1000, 950, 900, 850, 800, 750, 700, 650, 600, 550, 500, or less.

In all of the above embodiments, the peptides may be labeled with a detectable label. Any suitable detectable label can be used, including but not limited fluorescent labels. In one embodiment, the detectable labels for each peptide are distinguishable. Methods for detecting the label include, but are not limited to spectroscopic, photochemical, biochemical, immunochemical, physical or chemical techniques.

The compositions can be stored frozen, in lyophilized form, or as a solution. In one embodiment, the peptides may be immobilized on a surface of a solid support. Any suitable solid support may be used. Examples of such supports include, but are not limited to, microarrays, beads, columns, optical fibers, wipes, nitrocellulose, nylon, glass, quartz, diazotized membranes (paper or nylon), silicones, polyformaldehyde, cellulose, cellulose acetate, paper, ceramics, metals, metalloids, semiconductive materials, coated beads, magnetic particles; plastics such as polyethylene, polypropylene, and polystyrene; and gel-forming materials, such as proteins (e.g., gelatins), lipopolysaccharides, silicates, agarose, polyacrylamides, methylmethracrylate polymers; sol gels; porous polymer hydrogels; nanostructured surfaces; nanotubes (such as carbon nanotubes), and nanoparticles (such as gold nanoparticles or quantum dots). This embodiment facilitates use of the compositions in various detection assays.

In another aspect the disclosure provides methods for personalized treatment of breast cancer, comprising:

(a) performing sequence analysis of high-frequency cancer genes, or performing whole exome sequencing on DNA from a biological sample from a subject having breast cancer;

(b) identifying mutations in protein-encoding regions of the high-frequency cancer genes or the exome;

(c) creating a peptide array of mutant peptides comprising the mutations in protein-encoding regions of the high-frequency cancer genes or the exome, and optionally comprising wild-type counterparts of the mutant peptides;

(d) contacting the peptide array with a biological sample from the subject, for a time and under conditions to permit binding of antibodies in the serum (if present) to the mutant peptides and/or the wild-type counterparts thereof; and (e) detecting binding of antibodies in the serum to the mutant peptides and/or the wild-type counterparts thereof, thus identifying antigenic targets for therapy in treating the subject.

As disclosed in the examples that follow, the inventor has used the methods disclosed herein to identify 149 tumor antigens from human breast cancer patients, used to develop the compositions disclosed herein. While not being bound by any specific mechanism of action, the inventor proposes a general model of anti-cancer immunity wherein the disclosed methods help identify patient-specific tumor antigens in a timely fashion for precision immunotherapies. Such methods can thus be used to generate patient-specific peptide arrays which can then be screened using antibodies in a biological sample from the patient, including but not limited to serum, to identify antigenic targets that can be further targeted for treatment in the patient by, for example, administering antibodies against the identified targets to treat breast cancer.

Performing sequence analysis of high-frequency cancer genes, or performing whole exome sequencing on DNA, can be carried out using any suitable technique, including but not limited to those disclosed in the examples.

Similarly, identifying mutations in protein-encoding regions of the high-frequency cancer genes or the exome can be carried out using any suitable technique and comparison to any suitable reference genes, including but not limited to those disclosed in the examples.

The peptide arrays generated as described above can be used in additional methods. In one embodiment, the peptide arrays can be used to monitor breast cancer immunotherapy, the method comprising:

(a) contacting a biological sample from a subject who is undergoing or has undergone breast cancer therapy with the peptide array; and (b) determining an amount of antibodies against the one or more peptides in the bodily fluid sample;

wherein an increase in the amount of antibodies relative to a control, such as a baseline level of antibodies in a similar bodily fluid sample from the subject indicates efficacy of the breast cancer immunotherapy in the subject.

In one embodiment, the peptide arrays can be used to monitor breast cancer immunotherapy, the method comprising:

(a) contacting a biological sample from a subject who is undergoing or has undergone breast cancer therapy with the peptide array; and (b) determining an amount of antibodies against the one or more peptides in the bodily fluid sample;

wherein a decrease or no increase in the amount of antibodies relative to a control, such as a baseline level of antibodies in a similar bodily fluid sample from the subject indicates that the immunotherapy is ineffective in the subject.

Disclosed herein in a further embodiment, are methods to monitor breast cancer immunotherapy, comprising:

(a) contacting a biological sample from a subject who is undergoing or has undergone breast cancer therapy with the composition of any embodiment or combination of embodiments of the disclosure; and (b) determining an amount of antibodies against the one or more peptides in the bodily fluid sample;

wherein an increase in the amount of antibodies relative to a control, such as a baseline level of antibodies in a similar bodily fluid sample from the subject indicates efficacy of the breast cancer immunotherapy in the subject.

Disclosed herein in another embodiment, are methods to monitor breast cancer immunotherapy, comprising:

(a) contacting a biological sample from a subject who is undergoing or has undergone breast cancer therapy with the composition of any embodiment or combination of embodiments of the disclosure; and (b) determining an amount of antibodies against the one or more peptides in the bodily fluid sample;

wherein a decrease or no increase in the amount of antibodies relative to a control, such as a baseline level of antibodies in a similar bodily fluid sample from the subject indicates that the immunotherapy is ineffective in the subject.

The subject may be any suitable subject receiving breast cancer therapy, including but not limited to a human subject. As used herein, "breast cancer therapy" includes one or more of surgery to remove the primary breast tumor, radiation therapy, chemotherapy, and hormonal therapy.

A decrease in the amount of antibodies over time compared to a baseline level (i.e.: before breast cancer therapy initiation) indicates a favorable treatment response, while no decrease, or an increase, in antibody levels indicates a non-favorable treatment response. The methods can be carried out at any suitable time after breast cancer therapy begins as determined by attending medical personnel in light of all factors. In various non-limiting embodiments, the methods may be carried out at least 1 week, 2 weeks, 3 weeks, 1 month, 2 months, 3 months, 4 months, 5 months, 6 months, 7 months, 8 months, 9 months, 10 months, 11 months, 12 months, 18 months, 24 months, etc. after the beginning of therapy. As will be understood by those of skill in the art, the methods can be carried out any number of times for a given subject as deemed appropriate by attending medical personnel. Thus, the methods can be carried out 1, 2, 3, 4, 5, 6, 7 8, 9, 10, or more times for a given subject, to monitor the course of therapy. As will be understood by those of skill in the art, the methods can be carried out during the therapy, and can also be carried out after completion of the therapy, to monitor for possible breast cancer recurrence.

In all of the methods disclosed herein, the methods may include the use of additional antibody detection markers and controls as is appropriate for an intended use of the composition. The contacting can be carried out under any suitable conditions for promoting binding between the antibodies in the biological sample and the peptide array to form a binding complex that can be detected. Appropriate such conditions can be determined by those of skill in the art based on the intended assay, in light of the teachings herein. Similarly, any suitable additional steps can be used in the methods, such as one or more wash or other steps to remove unbound antibodies.

Any suitable detection technique can be used, including but not limited to enzyme linked immunosorbent assays (ELISA), bead based assay platforms such as the LUMINEX® systems, and 2-D array based assay platforms such as SEARCHLIGHT®. In one embodiment, the peptide arrays can be placed on a solid support, such as in a microarray, glass slide, membrane, microplate format or beads. The embodiment facilitates use of the compositions. Exemplary such assays are provided in the examples.

Similarly, any suitable biological sample can be used, including but not limited to a serum sample, plasma sample or blood sample from the subject. A "plasma sample" means blood plasma, the liquid component of blood, and is prepared, for example, by centrifugation of whole blood to remove blood cells. A serum sample is a plasma sample in which blood clotting factors have been removed.

In one embodiment, when no decrease is determined in the amount of antibodies relative to a baseline level of antibodies in a similar bodily fluid sample from the subject, the method may further comprise altering the breast cancer therapy being administered to the subject. Since the lack of antibody decrease indicates a non-favorable therapeutic outcome for the subject, this embodiment permits modifying the therapy as deemed appropriate by attending medical personnel (i.e.: increased dosage, change in treatment, etc.) to achieve a more favorable therapeutic outcome.

Examples

Recent advances in cancer immuno-therapeutics such as checkpoint inhibitors, chimeric antigen-receptor T cells, and tumor infiltrating T cells (TIL) are now significantly impacting cancer patients in a positive manner. Current reports indicate no more than 25% of cases result in complete remission. One of the limitations of these treatments is the identity of putative cancer antigens in each patient as it is technically challenging to identify of cancer antigens in a rapid fashion. Thus, identification of cancer antigens followed by targeted treatment will increase the efficacy of cancer immunotherapies.

We hypothesized that current immunomodulatory therapies are not highly effective for a large majority of cancer patients because 1) tumor antigens are not known, 2) strategies of boosting targeted anti-tumor response using tumor antigens is not a common treatment strategy, and 3) sufficient cooperation and stimulation between T, B, and dendritic cells are not promoted, and 4) a general strategy to relieve suppressive tumor microenvironment, such as checkpoint inhibition is not part of the standard therapies. To identify tumor-derived antigenic targets and to gain molecular insights into anticancer immunity, we have developed an integrative genomics-driven immunoproteomics platform (GDI). Using deep sequencing to identify mutations in the coding regions of 348 genes from 15 breast cancer patients, we designed personalized peptide microarrays. These microarrays contain mutant peptides and corresponding wild type counterparts. Incubating these personalized peptide microarrays with sera from respective patients revealed immunoreactive tumor antigens recognized by antibodies. In addition, we designed peptide microarrays based on high-frequency mutations extracted from two breast cancer studies and 9000 cancer genomes compiled in the COSMIC™ database, allowing us to identify high-frequency mutations that invoke immune response in cancer patients. Moreover, whole-genome sequencing and examination of personalized peptide microarrays of three breast cancer patients was carried out. Overall, we report the identification a total of 149 putative cancer antigens. We propose a strategy to eradicate cancer focusing on the GDI-based rapid identification of putative tumor antigens, monitoring the cancer patients' immune response, and utilization of tumor antigens in anticancer therapeutics.

Materials and Methods
Patient Sample Selection and Characterization

The study to analyze de-identified tumor tissues and sera samples from breast cancer and benign cancer samples were approved by the UCHC Institutional Review Board (IRB). De-identified patients' discarded materials, 15 tumor samples and 15 benign samples, were collected by the UCHC Tissue Biorepository Core, tumor samples and adjacent normal tissues were subjected to next generation genomic sequencing, and tumor associated variants (SNVs, insertions, deletions) were determined using the Genesifter™ software tool. Matching sera from these patients were used to test the presence of mutation-specific antibodies in patients' sera by mutant-peptide microarrays. Briefly, in-depth targeted genomic DNA sequencing of 348 genes was carried out in cancer patients' tissue samples. Since benign cancers tissue samples were not readily available for next generation sequencing experiments, mutation analysis was carried out only in the malignant cancer samples. From the 15 malignant cancer samples sequenced for 348 genes, three malignant cancer patients were subjected to whole exome sequencing for ~25,000 genes using cancer tissues and adjacent normal regions. Only the mutation detected specifically in the cancer tissues (after the comparative analysis with the adjacent normal tissues) from whole exome sequencing was then used to design the V5 peptide microarrays. Sera was collected from both malignant and benign cancer patients and tested for immunogenicity against mutant peptides using the V1-5 peptide microarrays. A minimum of two technical replicates were performed for each peptide microarray design.

Targeted Sequencing

A targeted SureSelectXT™ HiSeq sequencing study (Agilent Technologies, Danbury, Conn.) was designed to capture exome regions of 348 genes of interest in 15 breast cancer patients. The list of 348 genes was assembled from common breast cancer genes based on published reports; genes mutated in multiple breast cancer patient samples of recently published studies; genes with immunogenic mutant peptides, based on preliminary peptide chip results; genes with mutant spot intensities in the top 10%, based on preliminary chip results; additional recognized oncogenes; and interactors of transcription factors inducing pluripotent stem cells, retrieved from the Human Protein Reference Database. Custom baits for 348 genes were designed using SureDesign™, Agilent's online design tool. Approximately 3 ug of gDNA were extracted from each of 15 de-identified breast cancer patient tissue samples obtained from John Dempsey Hospital, University of Connecticut Health Center, with a NucleoSpin™ tissue kit (Macherey-Nagel). Library preparation and capture were then carried out by PerkinElmer with the extracted gDNA, using a SureSelectXT™ custom library and reagent kit purchased from Agilent Technologies.

The GRch37/hg19 Homo sapiens assembly was used in the design of the exome capture kit for the 348 genes. 68262 probes comprising a total of 2.7 Mbp provided bp coverage of 99.72%, with a probe tiling density of 4×. Target databases included RefSeq™, Ensembl™, CCDS™, Gencode™, VEGA™ and SNP™. The target region included coding exons of the 348 genes with an extension of 10 bps from the 3' and 10 bps from the 5' ends. Read length was 100 bps. Sequencing results were analyzed in the lab using PerkinElmer's online Genesifter™ tool. For each of the 15 breast cancer tissue samples, missense variants with an alternate read count >29 were selected for immunogenicity testing on personalized peptide chips.

Creating Peptide Arrays

In this study, four basic peptide chip designs (V1-V5) were developed and tested for differential binding affinity of mutant (mut) versus corresponding wild type (wt) peptides to antibodies in patient serum samples. Chip designs included personalized peptide arrays and three sets of diagnostic arrays. Fifteen personalized peptide chips (V1) contained duplicate sets of a variable number of wt-mut peptide pairs. Each personalized chip contained the unique set of filtered missense mutations identified in that patient's tumor sample in a SureSelectXT™ HiSeq sequencing study, paired with the wt counterparts, ranging from 460-746 wt-mut pairs among the 15 arrays. An additional set of commonly reported cancer mutations was added to each chip in a common, 'diagnostic' region at the bottom of the microarray.

In addition to the personalized arrays, three versions of diagnostic chips were designed. The initial diagnostic chip (V2) comprised triplicate sets of 1390 wt-mut peptide pairs. The second diagnostic chip (V3) contained a single set of 3071 wt-mut pairs, which merged the original unique wt-mut pairs from V2 with missense mutations from a more recent breast cancer study[20]. For the third diagnostic chip (V4), highly mutated sites from the COSMIC™ database were retrieved to create an array of 593 singlet wt-mut pairs. Filtering criteria for the retrieved mutations were (1) site count (i.e., total mutations at a given site) >17 and (2) specific mutation count >=10. Each V4 chip contained five identical arrays of 593 wt-mut pairs each.

Incubation of Peptide Microarrays

Each peptide microarray was first rehydrated for 10 min with 1 ml of standard buffer (0.5% Tween 20 in PBS pH7.4) in room temperature. Overnight incubation with blocking buffer (1% BSA, 0.5% Tween 20 in PBS pH7.4) was carried out at 4 degrees in continuous shaking at 200 rpms. Peptide arrays were washed 3×1 min with standard buffer and incubated with the corresponding patient sera diluted in staining buffer (1:25 dilution in staining buffer—0.5% Tween 20, 0.1% BSA in PBS pH7.4). We had tested 1:10, 1:25, 1:50, and 1:500 dilutions using peptide microarrays. We found that although the lowest dilution (1:10) and the highest dilution (1:500) showed similar qualitative results, the best quantification for mutant: wild type ratios can be achieved at 1:25 serum dilution. Therefore, after careful analysis of the data from multiple dilutions, we have chosen to use 1:25 dilution as a way to assay for detection of breast cancer tumor antigens. Sera from each patients are diluted in staining buffer incubated with peptide microarrays for overnight at 4 degrees Celsius. Standard buffer was then used for 3 consecutive washes (3×10 min each) in room temperature after the overnight incubation. Next, peptide microarrays were incubated with goat anti-human IgG secondary antibody CY3-bound (1:1000 in staining buffer) for half an hour, followed by 3 more washes with standard buffer and a final wash with deionized water. The peptide microarrays were then dried, scanned using a GenePix™ 4000 B scanner and analyzed using GenePix™ Pro 6.0 software, converting each spot into its mean and median pixel intensities.

Assessing Differential Mutant Binding Affinity

We first tested and validated the peptide microarray platform variability by generating peptide microarrays with increasing number of positive control peptides (1, 2, 3, 6, and 9 spots each), incubated the microarrays with patients' sera, and quantified the results to establish the spot-to-spot variation. Across multiple peptides, we found that the peptide microarrays are highly reproducible and standard deviations range between 5-20%.

Second, in order to achieve a robust statistical selection of immunogenic peptides, we utilize the power law global error model (PLGEM) statistics[26]. Briefly, fluorescent intensities of wild type versus mutant peptide spots (for each duplicate set of wt-mut pairs) were compared using the PLGEM in order to identify statistically significant intensity differences. PLGEM software was downloaded from www.bioconductor.org and run in-house. A cutoff p-value of 0.01 was used as an initial filter for significance. Additionally, multiple chips were incubated with the same serum and only mutations showing the same immunogenic trend in two or more chips were retained in the significance list.

Immunoreactive mutant and wild type peptides were also assessed using the Kyte-Dolittle Algorithm to rule out physiochemical-based non-specific interactions with sera. We found that immunoreactivity is independent of the GRAVY scores, indicating the specificity of antibody interaction with peptide sequences. Multiple biological and technical replicates using peptide microarrays revealed consistent results. For the personalized peptide chips (V1), fluorescent intensities of wt versus mut peptide spots within each duplicate set of wt-mut pairs were compared using the power law global error model (PLGEM) in order to identify statistically significant intensity differences[26]. For the first diagnostic chip (V2), a t-test was used to compare fluorescent intensities within each triplicate set of wt-mut pairs. A cutoff p-value of 0.05 was used as the initial filter. The second and third diagnostic chips (V3-V4) had no replicate spots. The whole exome chips (V5) were synthesized with duplicate spots for the wild type and mutant peptides. In this case, the initial test for significance was a check that there was no overlap between 99% confidence intervals (CI) around the mutant mean intensity and the wt mean intensity for each wt-mut pair of spots. CI was computed as the raw mean+/−z(0.01)*stdev/sqrt(576), where 576=number of pixels in computation of raw mean, stdev is the standard deviation of the mean of 576 pixel intensities, and z(0.01)= 2.575[27].

For all microarrays, a second filter was then applied, retaining only those mutants whose mut/wt mean and median ratios were both greater than 2.0 (>1.5 for V4, V5). Requiring both mean and median ratios to pass the filter reduced the number of artifacts which remained in the significance list. Artifacts were caused mainly by intensity spillover from adjacent spots, or extraneous spots on the chip. Additionally, where multiple chips were incubated with the same serum, only mutations showing the same immunogenic trend in two or more chips were retained in the significance list. Once the initial filters were applied, a final visual inspection of the significant spots was required to remove any remaining entries whose intensity differences were due to artifacts. No statistical difference in the amount of reactive peptides per gene between the 348 gene array and whole exome array was observed.

Multiplex PCR Amplification and Next Generation Sequencing of IgH and IGKL CDR3 Sequences To generate the template library for the Illumina HiSeq™ machine, a multiplex PCR system was designed to amplify rearranged IgH and IGKL loci from genomic DNA using methods previously described[28]. Multiple consensus forward primers, each specific to a functional IgH V, IgL V, and IgK V segments are amplified using consensus reverse primers from J segments. The amplified products are used for the library construction and sequencing using the Illumina HiSeq System, which generates reads of length 110 bp and covers the entire range of CDR3 lengths, sequencing from the J to the V region. All sequencing was performed at Adaptive Biotechnologies Corp.

Preprocessing of Genome Analyzer Sequence Data

Raw HiSeq™ sequence data were preprocessed to remove errors in the primary sequence of each read and to compress the data. Among the three cancer tissue samples analyzed, approximately 10-13% of the sequences from IgH and 37-42% of the IgKL sequences from the HiSeq™ were technical failures and were removed by a complexity filter and a nearest neighbor algorithm was used to collapse the data into unique sequences as described[29]. Data analysis was performed as previously described[28].

Results

Development of Genomic-Driven Immunoproteomics Platform

We have collected and performed deep sequencing of high-frequency cancer genes. The variants identified from each patient served as a template to design a patient-specific peptide array. This personalized array then served as an identification platform for the discovery of antigenic targets, using serum from each corresponding patient.

Thus, genomic variants on coding exons of 348 frequently mutated cancer genes from 15 breast cancer patients' tumors were subjected to exome capture followed by deep sequencing, resulting in a mean read-depth of over 900 (Table 2). This deep sequencing strategy allowed the detection of mutations in regions of cancer tissue even when the distribution of cancer cells was extremely low. As a result, all 348 genes were successfully captured and sequenced, resulting in the identification of 460-746 unique missense variants from each patient, including variants in cancer driver genes such as BRCA1, BRCA2, TP53, MLL3, and NCOR1. Indeed, a substantial number of new variants were identified in breast cancer through the deep sequencing method. Although the exact function of the detected variants in cancer is not known, their identification permitted us to investigate their potential antigenicity in each patient.

TABLE 2

Summary of immunogenic variant peptides identified by V1 peptide microarrays:
Personalized peptide microarrays were incubated with corresponding patients' sera, peptides were quantified, and the PLGEM statistical analysis was calculated (as described in the Materials and Method Section). Note that only limited numbers of putative tumor antigens were identified from over 2000 unique peptides tested.

| Patient | Cancer Genes | Immunoreactivity (MT/WT) Intensities | Codon | Experiment |
|---|---|---|---|---|
| Patient 1 | MUC17 | 5.25 | T959A | NextGenSeq |
| Patient 1 | MUC17 | 4.63 | T2786A | NextGenSeq |
| Patient 5 | PCSK5 | 3.03 | T1343M | NextGenSeq |
| Patient 1 | NCOR1* | 2.54 | K178N | NextGenSeq |
| Patient 5 | INF2L2 | 2.31 | E79K | NextGenSeq |
| Patient 1 | OBSCN | 2.18 | V1600D | NextGenSeq |
| Patient 3 | IALPK | 2.18 | P1449S | NextGenSeq |
| Patient 2 | MUC17 | 2.06 | S1083P | NextGenSeq |
| Patient 4 | TTN | 2.02 | K1155E | NextGenSeq |
| Patient 1 | BRCA1* | 1.98 | E1038G | NextGenSeq |

*Driver Cancer Genes

Discovery of Nine Genomically Verified Breast Putative Cancer Antigens Using Personalized Peptide Microarrays In the next step, translation of the genomic sequencing data into a patient's personalized immunological assessment, termed GDI, was achieved through an innovative platform of personalized peptide microarrays, each one designed for a specific patient based on that patient's set of sequenced variants. These personalized peptide microarrays, comprising 460-746 duplicate pairs of 15-mer wild type (wt) and corresponding mutant (mut) peptides, were synthesized using amino acid particle-based technology, which allows the generation of thousands of unique peptides directly on a single glass slide. Patient-specific personalized peptide microarrays, termed V1 chips, were tested against matching patients' sera to identify the antigenic mutant peptides among those mutations, discovered through genomic sequencing. Antibodies present in serum from patient 1 reacted specifically to five mutant peptides, but not to their wt counterparts. Quantification of each of the five peptide spots on the personalized peptide array and statistical analysis indicated significant immunoreactivity to BRCA1 (E1038G), NCOR1 (K178N), OBSCN (V1600D), and MUCIN 17 (T2786A and T959A). Out of 2047 variants tested altogether among 15 breast cancer patients, we found nine genomically verified mutations that invoked a strong immune response (Table 2). These results indicate that immunogenic variants are relatively rare among the variant landscape of an individual cancer genome, so that a systematic method for their identification is crucial. Using the GDI platform, detection of immunogenic mutations, specific to each cancer patient, can be achieved rapidly.

Detailed analysis of peptide microarrays revealed that genomic variants shared among multiple patients failed to invoke a common antibody-mediated immune response in all the patients carrying these mutations. For example, the BRCA1 (E1038G) genomic mutation was found in five breast cancer patients; yet, the antibody-mediated immune response was invoked only in Patient 1. Similarly, NCOR1 (K178N) mutation was found in all 15 patients, but invoked an immune response in only one patient. Additional examples were observed for OBSCN, MUCIN17, IALPK, TTN, and PCSK5; in each of these cases of shared genomic variants, most patients failed to invoke an antibody-mediated immune response. These results highlight that a defective immune response against common mutant proteins predominates in most cancer patients.

Identification of 53 Putative Cancer Antigens Using Publically Available Cancer Databases In order to identify additional genome-wide breast cancer associated mutations beyond the 348 genes examined, three diagnostic peptide microarrays were designed and tested. Two diagnostic microarrays, namely V2 and V3 chips, were designed based on mutations that have been identified by two large scale genomic sequencing studies in breast cancer. The third diagnostic microarray (V4) was designed utilizing high-frequency mutations extracted from over 9000 cancer genomes curated in the Cosmic database. Testing the diagnostic peptide microarrays with sera from 15 breast cancer patients and 15 benign cancer patients resulted in the identification of 53 additional genomic mutations that invoked an immune response. Thus, combining positive data from V1-V4 microarrays resulted in the identification of 62 putative cancer antigens, among which 53 are high-frequency mutation sites.

Whole Genome GDI Analysis of Three Cancer Patients Resulted in Identification of 35-50 Immunogenic Putative Cancer Antigens Per Patient Since 348 genes represent a small fraction of 25,000 genes of the human genome, we tested the presence of tumor antigens at a whole protein-coding genome/exome level. Thus, we sequenced the whole exomes of three breast cancer tissues and adjacent normal regions, identified mutations that are exclusively present in the tumor tissues, and designed personalized peptide microarrays populated with mutant and corresponding wild type peptides based on the genomic sequencing. We found that wild type and mutant peptides derived from genomic sequencing of normal and cancer regions of patient 1 (585 mutations) and patient 2 (576 mutations) resulted in peptides that can fit into one slide. However, genomic DNA sequencing of patient 6 resulted in the identification of 3775 mutations, resulting in the populating these mutations on two microarrays. In addition, we also populated the peptide microarrays with high frequency mutations from the COSMIC™ database. Subsequent testing of these peptide microarrays using sera from respective patients were carried out. When compared to the sequencing of 348 genes, whole exome sequencing resulted in increased number of genomic mutations that showed strong reaction to cancer-associated mutations. In total, 35-50 immunogenic mutant peptides were identified in each patient, among which substantial increase in the total number of putative tumor antigens/antigenic peptides that are verified by whole genomic sequencing (Table 1). Detailed analysis of these whole exome microarrays revealed immune response against mutant peptides derived from the patient as well as from the COSMIC database (Table 1). In total, combining data from V1-V5 arrays, we identified 149 immunogenic peptides that invoke immune response in cancer patients, among which 20 are insertions, 59 are deletions, and 70 are SNVs (Table 1). These results reveal that there is a wide-spread antibody response targeting mutant amino acids including the single-nucleotide variants.

DISCUSSION

This study identified genomic mutations on the protein coding exons of breast cancer patients and detected immune reactivity against subset of these mutations using peptide microarrays. The first sequencing study, focused on 348 commonly mutated cancer associated genes in 15 breast cancer patients, revealed that only a small subset (nine) of mutated genes are immunologically reactive to antibodies present in patient sera. Expanding the number of investigated genes to the whole exome-level and testing for antibody response revealed much higher number of putative cancer antigens in all three patients examined; 35 genomically verified mutations were found to have strong immune response. These results suggest that although there are hundreds to thousands of mutations in the protein coding regions of cancer genomes, only a minor subset of mutant proteins can invoke antibody-mediated immune response. This phenomenon may be due to multiple influencing factors such as the abundance of mutant proteins in cancer cells, the affinity of mutant peptides to the expressed HLA receptors, presence of efficient antigen presentation and lymphoid circulation, and overcoming the immune suppressive tumor microenvironment. Interestingly, when high-frequency cancer-associated mutations from COSMIC™ database and from two other breast cancer studies were examined, additional putative breast cancer antigens were discovered (Table 1). Overall, these results support the hypothesis that widespread genomic mutations in protein coding exons of human breast cancer patients can invoke an immune response targeted against the mutant peptides. Specifically this investigation has led to the identification of 149 cancer-specific immunogenic antigens, providing strong evidence that mutant proteins can be recognized by the immune system, and these invoke an antibody-mediated immune response (Table 1).

Interestingly, this investigation resulted in the identification of a number of new cancer associated mutations not previously reported in the COSMIC™ database or other studies. One possible explanation for this observation is due high read-depth of genomic sequencing, which allows sensitive detection of mutations. This finding was also confirmed by sequencing germline DNA from normal tissues of three patients and compared the data with sequence data from matching tumor DNA. It is only beginning to be recognized by leading cancer researchers that there is a so called "dark matter" in the cancer genome, referring to the gene mutations that are commonly missed because of low sequencing depth typically used. Consistent with this notion, when ultra-deep sequencing was performed on normal eyelids of five individuals sequencing at 500 read-depth/gene on 74 genes, a number of new mutations on oncogenes were discovered.

This investigation also introduces a discovery platform, termed the GDI, that allows rapid translation of mutational profiles generated from genomic sequencing of cancer patients into an immunological test, which can be used to assess patients' immunological profile as well as discovering putative antigenic targets. Further, this platform is useful for monitoring the immunological response of different types of existing immunotherapies/checkpoint inhibition such as anti-CTLA-4, anti-PDL-1, and anti-PD-1. Currently, patients undergoing these immunotherapies are monitored for tumor shrinkage, approximately several weeks after treatment by computed tomography (CT) or magnetic resonance imaging (MRI). While imaging modalities are useful to determine the response rate, immunological status and the correct dosage cannot be assessed accurately and fine-tuned for optimal response. Using the GDI methodology can potentially provide direct assessment of cancer patients' immune status. For example, patients who do not show detectable antibody response against cancer-associated mutant proteins before or after checkpoint inhibition therapies are likely to be poor candidates for continued treatment with these agents. On the other hand, patients who show no immune response against mutant proteins before the treatment but mount a strong response after checkpoint inhibition therapies may be good candidates for continued treatment. Further, immunological readouts for patient-specific cancer mutations can be measured before, during and after immunotherapy using this platform using a simple blood test, so that optimal tumor killing can be correlated with the quantifiable signals measured by GDI-based personalized peptide arrays. Finally, tracking T-cell mediated immune response against the patient-specific mutants throughout treatment of checkpoint inhibition is quite challenging. Since antibody-mediated B cell response requires T-helper cells recognizing the tumor antigen and stimulating specific B cell clones, quantification of antibody response may assist in determining the proper checkpoint inhibitor dosage in a patient specific manner.

Since the GDI platform measures antibody-mediated immune response directly against mutant proteins (which also requires $T_H$ cell-mediated B cell activation), the use of GDI-based peptide microarray as a companion diagnostic blood test will provide additional quantifiable measurements, such as the number and extent of antibody binding to mutant proteins. Frequent monitoring of cancer patients before, during, and after the checkpoint inhibition using the GDI platform will allow standardization of immunotherapies by assessing quantifiable measurements of patients' immune reaction against tumor-specific mutant proteins. The GDI platform is also useful for the checkpoint inhibitor drug dosing of individual cancer patients at the immunological level, and may allow more accurate categorization of true responsive versus non-responsive patients.

The personalized peptide microarrays that we have utilized for the first time have application for immunotherapy, such as selecting vaccine epitopes for cancer patients. Previous efforts to treat cancer using peptide vaccines have not been widely efficacious, possibly because there is not a straightforward assay to select strong antigenic epitopes relevant to each patient. Utilizing antigenic peptides based on the GDI method is an efficient way to select relevant vaccine targets. In patients that respond to mutations immunologically, boosting the immune system with a peptide vaccine containing antigenic targets may help eliminate the tumor directly. Further, peptide microarrays can be used to monitor the immune response during vaccine-based immunotherapy in cancer patients.

Examination of tissue sections of all patients revealed that there is a strong correlation between presence of immune cell infiltration in the cancer tissues and antibody response seen at the peptide microarray level.

Based on our study design, we were able to identify and evaluate two interesting categories of antibody response— one being the response against mutant proteins that are found in the genomic DNA of tumor tissues (from V1 and V5 personalized chips), and the other being the response against mutant proteins not detected in the genomic DNA of tumor tissues examined (from V2-4 diagnostic chips). For example, although four variants of TP53 (P72R, R248Q, D281H, Y234N) were identified in the deep sequencing of 15 breast cancer tissue samples, none of these genomic mutants of TP53 was found to invoke an immune response in the breast cancer patients examined. However, when additional site-specific and frame-shift mutations of TP53 and CDKN2A reported in the COSMIC database were tested in diagnostic peptide microarrays, immune response against nine TP53 site-specific mutations and nine frame-shift mutations, as well as four CDKN2A frame-shift mutations were detected in patient serum, even though these mutations were not detected in the DNA from breast cancer tissues that were sequenced in this study (Table 1). The reason for detecting antibody responses in cancer patients against mutant proteins not verifiable at the exomic DNA level is unclear at present. One likely explanation is that while DNA is not mutated, multiple RNAs are mutated due to errors in RNA editing mechanisms. Also, RNA translational errors may result in mutated proteins. Indeed, an integrative study on human disease tissues at the DNA, RNA, protein, and immunological levels revealed similar phenomenon[44]. Similar findings have also been reported in a number of large-scale cancer omics studies, in which differences in DNA and RNA mutations have been documented[45].

Another possible explanation is that mutations arising from other organs and tissues over the life span of patients, which invoked systemic antibody response against these mutant proteins produced from memory B cells, may linger in patients' bloodstream. In this scenario, genomic sequencing of cancer tissues will not capture the entire mutation repertoire in many other tissues and will be discordant with antibody responses. Indeed, sequencing of normal eyelids from five subjects revealed many oncogenic mutations including TP53 and CDKN2A genes, indicating that widespread DNA mutations is a common occurrence[34]. Further, due to the well know phenomena of clonal drifting of cancer cells, immune system may only eliminate a subset of cancer clones. In this scenario, antibody response may continue to be present in the patient's sera, as detected by peptide microarrays, while the genomic mutation signature may have been eradicated by the immune system.

It is interesting that when we first examined immune response against mutant proteins from 348 genes, we found that very few mutant peptides invoked immune response in breast cancer patients. However, when we analyze the whole exomes of three patients and tested all the mutations on microarrays, we found substantially more immune reactive mutant peptides. Corresponding wild type peptides did not show detectable level of immune reactivity. These results suggest that immune response against mutant peptide is specific and unlikely to be due to nonspecific autoantibody binding.

In summary, our results indicate that antigenic targets of frequently mutated cancer genes can be screened in a high-throughput manner by the GDI platform described in this paper. The combination of deep genomic sequencing and personalized peptide arrays based on sequencing results offers a novel platform for uncovering new cancer-specific antigenic targets and may help identify effective anti-cancer treatment regimens. The high-throughput assay of GDI-based peptide microarrays has the distinct advantage of streamlined antigenic peptide identification and may offer a seamless translation from genomics sequencing data into actionable blood test that can quantify and monitor immune response of patients.

REFERENCES AND WEB SITES

1. June, C., Rosenberg, S. A., Sadelain, M., Weber, J. S., et al., T-cell therapy at the threshold. Nat. Biotechnol. 2012, 30, 611-4.
2. Pardoll, D. M. Immunology beats cancer: a blueprint for successful translation. *Nat. Immunol.* 2012, 13, 1129-1132
3. Leach, D. R., Krummel, M. F., Allison, J. P. Enhancement of antitumor immunity by CTLA-4 blockade. *Science* 1996, 271, 1734-1736.
4. Frankel, J. C., The dizzying journey to a new cancer arsenal. *Science* 2013, 340, 1514-1518.
5. Frankel, J. C., Immune therapy steps up the attack. *Science* 2010, 330, 440-443.
6. Topalian, S. L., Hodi, S. F., Brahmer, J. R., Gettinger, S. N., et al., Safety, activity, and immune correlates of anti-PD-1 antibody in cancer. *N. Engl. J. Med.* 2012, 366, 2443-2454.
7. Wolchok, J. D., Kluger, H., Callahan, M. K., Postow, M. A., et al., Nivolumab plus ipilimumab in advanced melanoma. *N. Engl. J. Med.* 2013, 369, 122-133.
8. Rosenberg, S. A., Restifo, N. P., Adoptive cell transfer as personalized immunotherapy for human cancer. Science 2015, 348, 62-8.
9. Vogelstein, B., Papadopoulos, N., Velculescu, V. E., Zhou, Sh., et al., Cancer genome landscapes. *Science* 2013, 339, 1546-1558.
10. Beal M. A., Glenn, T. C., Somers, C. M., Whole genome sequencing for quantifying germline mutation frequency in humans and model species: cautious optimism. *Mutat. Res.* 2012, 750, 96-106
11. Mertes, F., Elsharawy, A., Sauer, S., van Helvoort, J. M, et al., Targeted enrichment of genomic DNA regions for next-generation sequencing. *Genomics* 2011, 10, 374.
12. Linnebacher, M., Tumor-infiltrating B cells come into vogue. World J Gastroenterol 2013, 19, 8-11.
13. Erdag, G., Schaefer, J. T., Smolkin, M. E., Deacon, D. H., et al., Immunotype and immunohistologic characteristics of tumor-infiltrating immune cells are associated with clinical outcome in metastatic melanoma. Cancer Res. 2012, 72, 1070-1080.
14. Nelson, B. H., CD20+ B cells: the other tumor-infiltrating lymphocytes. J. Immunol. 2010, 185, 4977-4982.
15. Schmidt, M., Bohm, D., von Tome, C., Steiner, E., et al., The humoral immune system has a key prognostic impact in node-negative breast cancer. Cancer Res. 2008, 68, 5405-5413.
16. Nielsen J. S., Sahota, R. A., Milne, K., Kost, S. E., et al. CD20+ tumor-infiltrating lymphocytes have an atypical CD27-memory phenotype and together with CD8+ T cells promote favorable prognosis in ovarian cancer. Clin. Cancer Res. 2012, 18, 3281-3292.
17. Lee, H. J., Kim, J. Y., Park, I. A., Song, I. H., et al. Prognostic Significance of Tumor-Infiltrating Lymphocytes and the Tertiary Lymphoid Structures in HER2-Positive Breast Cancer Treated With Adjuvant Trastuzumab. Am. J. Clin. Pathol. 2015, 144, 278-288.
18. Curtis, C., Shah, S. P., Chin, S. F., Turashvili, G., et al., The genomic and transcriptomic architecture of 2,000 breast tumours reveals novel subgroups. Nature 2012, 486, 346-352.

19. The Cancer Genome Atlas Network. Comprehensive molecular portraits of human breast tumours. Nature 2012, 490, 61-70.
20. Ellis, M. J., Ding, L., Shen, D., Luo, J., et al., Whole-genome analysis informs breast cancer response to aromatase inhibition. Nature 2012, 486, 353-360.
21. Sjoblom, T., Jones, S., Wood, L. D., Parsons W. D., et al., The consensus coding sequences of human breast and colorectal cancers. Science 2006, 314, 268-274.
22. Takahashi, K., Tanabe, K., Ohnuki, M., Narita, Megumi., et al., Induction of pluripotent stem cells from adult human fibroblasts by defined factors. Cell 2007, 131, 861-872.
23. Yu, J., Vodyanik, M. A., Smuga-Otto, K., Antosiewicz-Bourget, J., et al., Induced pluripotent stem cell lines derived from human somatic cells. Science 2007, 318, 1917-1920.
24. Jones, S., Zhang, X., Parsons, W. D., Lin, J. Ch., et al. Core signaling pathways in human pancreatic cancers revealed by global genomic analyses. Science 2008, 321, 1801-1806.
25. Parson, D. W., Jones, S., Zhang, X., Lin, J. Ch., et al., An integrated genomic analysis of human glioblastoma multiforme. Science 2008, 321, 1807-1812.
26. Pavelka, N., Pelizzola, M., Vizzardelli, C., Capozzoli., et al., A power law global error model for the identification of differentially expressed genes in microarray data. BMC Bioinformatics 2004, 5, 203-214.
27. Johnson, J. Elementary Statistics, 5th Edition. PWS-KENT Publishing Company, Boston (1988).
28. Larimore, K., Mccormick. M. W., Robins, H., Greenberg, P., Shaping of Human Germline IgH Repertoires Revealed by Deep Sequencing. J. Immunology 2012, 189, 3221-3230.
29. Robins, H. S., Campregher, P. V., Srivastava, S. K., Wacher, A., et al. Comprehensive assessment of T-cell receptor beta-chain diversity in alphabeta T cells. Blood 2009, 114: 4099-4107.
30. Gundry, M., Vijg, J., Direct mutation analysis by high-throughput sequencing: from germline to low-abundant, somatic variants. *Mutat. Res.* 2012, 729, 1-15.
31. Biankin A. V., Waddell, N., Kassahn, K. S., Gingras M. C., et al., Pancreatic cancer genomes reveal aberrations in axon guidance pathway genes. *Nature* 2012, 491, 399-405
32. Forbes, S. A. et al. COSMIC: mining complete cancer genomes in the Catalogue of Somatic Mutations in Cancer. *Nucl. Acids Res.* 39 (suppl 1), D945-D950 (2011).
33. Beyer, M., Nesterov A., Block, I., Konig, K., et al., Combinatorial synthesis of peptide arrays onto a microchip. *Science* 2007, 318, 1888.
34. Martincorena, I., Roshan, A., Gerstung, M., Ellis, P., et al. High burden and pervasive positive selection of somatic mutations in normal human skin. Science 2015, 348, 880-886.
35. van Rooij, N., van Buuren, M. M., Philips, D., Velds, A., et al. Tumor exome analysis reveals neoantigen-specific T-cell reactivity in an ipilimumab-responsive melanoma. J. Clin. Oncol.
2013, 31, 439-42.
36. Chalmers, Z. R., Connelly, C. F., Fabrizio, D., Gay, L., et al. Analysis of 100,000 human cancer genomes reveals the landscape of tumor mutational burden. Genome Medicine 9:34 (2017)
37. Le, D. T., Uram, J. N., Wang, H., Bartlett, B. R., et al. PD-1 Blockade in tumors with mismatch-repair deficiency. N Engl J Med. 372:2509-20 (2015)
38. Rizvi, N. A., Hellmann, M. D., Snyder, A., Kvistborg, P., et al. Cancer immunology. Mutational landscape determines sensitivity to PD-1 blockade in non-small cell lung cancer. Science. 2015, 348:124-8.
39. Snyder, A., Makarov, V., Merghoub, T., Yuan, J., et al. Genetic basis for clinical response to CTLA-4 blockade in melanoma. N Engl J Med. 2014; 371:2189-99.
40. Rosenberg, S. A., Yang, J. C. & Restifo, N. P. Cancer immunotherapy: moving beyond current vaccines. *Nat. Med.* 10, 909-915 (2004).
41. Schumacher, T. et al. A vaccine targeting mutant IDH1 induces antitumour immunity. *Nature* 512, 324-327 (2014).
42. Tran, E. et al. Cancer immunotherapy based on mutation-specific CD4+ T cells in a patient with epithelial cancer. *Science* 344, 641-645 (2014).
43. Jiang, Q., Crews, L. A., Holm, F., Jamieson, C. H. M. RNA editing-dependent epitranscriptome diversity in cancer stem cells. Nature Reviews Cancer (2017) doi: 10.1038/nrc.2017.23
44. Qendro, V., Bugos, G. A., Lundgren, D. H., Glynn, J., et al. Integrative proteomics, genomics, and translational immunology approaches reveal mutated forms of Proteolipid Protein 1 (PLP1) and mutant-specific immune response in multiple sclerosis. Proteomics. 2017 March; 17(6). doi: 10.1002/pmic.201600322.
45. Mertins, P., Mani, D. R., Ruggles, K. V., Gillette, M. A., et al. Proteogenomics connects somatic mutations to signalling in breast cancer. Nature 534, 55-62 (2 Jun. 2016) doi:10.1038/nature18003

---

I claim:

1. An isolated composition, comprising at least 25 mutant peptides selected from the group consisting of SEQ ID NOS: 1-82, 84-91, and 93-149, or polypeptides comprising the mutant peptides; wherein the composition comprises mutant peptides encoded by 10 or more genes and wherein the mutant peptides are fluorescently labeled.

2. The isolated composition of claim 1, wherein the composition further comprises one or more wild type peptides corresponding to the mutant peptides, or polypeptides comprising the wild type peptides.

3. The isolated composition of claim 2, wherein the composition further comprises 25 or more wild type peptide counterparts to the mutant peptides, or polypeptides comprising the wild type peptides.

4. The isolated composition of claim 2, wherein the total number of mutant and wild type peptides, or polypeptides comprising the mutant and wild type peptides, is 100,000 or less.

5. The isolated composition of claim 2, wherein the total number of mutant and wild type peptides, or polypeptides comprising the mutant and wild type peptides, is 1000 or less.

6. The isolated composition of claim 1, wherein the mutant peptides are immobilized on the surface of a solid support.

* * * * *

SEQUENCE LISTING

```
<160> NUMBER OF SEQ ID NOS: 149

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Ser Met Arg Ile Leu Ser Ala Leu Val Gln Phe Val Lys Gly Pro
1               5                   10                  15

<210> SEQ ID NO 2
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 2

Ser Val Leu Arg Ser Ser Gln Cys Gln Pro Val Met Arg Arg Met
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Pro Ala Glu Gly Arg Lys Pro Arg Val Val Met Phe Leu Gln Pro
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Asp Cys Gln Leu Lys Pro Ala Glu Thr Ala Cys Arg Asp Ser Ser
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Ser Ser Ser Glu Met Thr Asn Thr Ser Asp Thr Leu Asn Ile Glu
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Gly His Glu Ala Glu Ile Gln Ser Ala Ile Leu Gln Val Pro Cys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Ala Glu Val Lys His Leu His His Leu Leu Lys Gln Leu Lys Pro
1               5                   10                  15

<210> SEQ ID NO 8
<211> LENGTH: 15
<212> TYPE: PRT
```

```
<213> ORGANISM: Artificial Sequence
<220> FEATURE:
<223> OTHER INFORMATION: Synthetic

<400> SEQUENCE: 8

Thr Gly Cys Asn Pro Lys Ser Met Leu Val Leu His Arg Gly Met
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Asp Ser Ala Asn Thr Leu Gln Ile Ala Glu Arg Lys Asp Trp Asn
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Leu Asp Leu Glu Ala Thr Ile His Lys Val Val Lys Ile Tyr Asp
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Leu Asp Arg Pro Gly Asn Ser Thr Pro Ser Arg Val Pro Ser Arg
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic

<400> SEQUENCE: 12

Arg Ala Gly Arg Met Gly Gly Arg His Pro Ser Trp Pro Trp Thr
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic

<400> SEQUENCE: 13

Glu Leu His Leu Asp Asn Asn Asn Leu Ala Arg Val Pro Ser Gly
1               5                   10                  15

<210> SEQ ID NO 14
<211> LENGTH: 15
<212> TYPE: PRT
<213> ORGANISM: Artificial Sequence
```

```
<220> FEATURE:
<223> OTHER INFORMATION: Synthetic

<400> SEQUENCE: 14

Gly Asp Phe Gly Leu Ala Thr Glu Lys Ser Arg Trp Ser Gly Ser
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic

<400> SEQUENCE: 15

Ile Arg Glu Asn Val Phe Lys Gly Ala Ser Ser Ser Asn Ile Asn
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Pro Thr Pro Ala Ser Pro Ala Ala Arg Pro Thr Ser Cys Ser Thr
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic

<400> SEQUENCE: 17

Glu Ala Ala Thr Arg Ala Glu Val His Gly Ser Pro Glu His His
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic

<400> SEQUENCE: 18

Arg Gly Gln Pro Gly Pro Val Asp Pro Gln Gly Tyr Asn Gly Pro
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic

<400> SEQUENCE: 19

Arg Arg Met Met Arg Thr Lys Met Arg Met Arg Arg Met Arg Arg
1               5                   10                  15

<210> SEQ ID NO 20
<211> LENGTH: 15
<212> TYPE: PRT
<213> ORGANISM: Artificial Sequence
<220> FEATURE:
```

```
<223> OTHER INFORMATION: Synthetic

<400> SEQUENCE: 20

Arg Arg Lys Met Ser Pro Ala Arg Pro Arg Thr Ser Cys Arg Ala
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic

<400> SEQUENCE: 21

Met Met Arg Thr Lys Met Arg Met Arg Arg Met Arg Arg Thr Arg
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic

<400> SEQUENCE: 22

Met Arg Met Arg Arg Met Arg Arg Thr Arg Arg Lys Met Arg Arg
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic

<400> SEQUENCE: 23

Asn Pro Pro Ala Pro Ala Ala Thr Pro Thr Gly Pro Ala Ala Asn
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24

Asn Cys Ala Asp Pro Ala Thr His Pro Thr Arg Ala Arg Arg Cys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic

<400> SEQUENCE: 25

Ser Ala Arg Val Ala Glu Leu Thr Ala Pro Thr Pro Pro Leu Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Synthetic
```

<400> SEQUENCE: 26

Arg Ala Arg Arg Cys Pro Gly Gly Leu Pro Gly His Ala Gly Gly
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic

<400> SEQUENCE: 27

Gly His Ala Gly Gly Ala Ala Pro Gly Arg Gly Ala Ala Gly Arg
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic

<400> SEQUENCE: 28

Ala Ser Thr Arg Arg Pro Ser Thr Ser Ala Pro Thr Ser Thr Arg
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

Pro Thr Ser Thr Arg Pro Pro Ser Thr Thr Ser Ser Trp Pro Thr
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic

<400> SEQUENCE: 30

Arg Ala Arg Asp Val His Arg His Gln Arg Leu His Arg Pro Gly
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Leu His Arg Pro Gly Arg Leu Gln Arg Arg Val Pro Gly Arg Pro
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic

```
<400> SEQUENCE: 32

Ala Ala Gly Glu Gly Gln Gly Gly Arg Gly Pro His Gly Arg Arg
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic

<400> SEQUENCE: 33

Arg Thr Glu Thr Pro Pro Lys Val Arg Trp Pro Trp Val Pro His
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic

<400> SEQUENCE: 34

Ile Thr Asp Phe Gly His Ser Glu Ile Leu Gly Glu Thr Ser Leu
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic

<400> SEQUENCE: 35

Val Glu Val Asp Val Asp Glu Ser Asn Gln Glu Gln Val Ala Asp
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic

<400> SEQUENCE: 36

Ala Lys Pro Ser Ser Phe Phe Cys Arg Cys Arg Arg Glu Tyr Arg
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic

<400> SEQUENCE: 37

Thr Cys Arg Cys Gly Val Pro Ala Cys Ser His Val Pro Met Arg
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic

<400> SEQUENCE: 38
```

His Ala Glu Cys Pro Pro Ala His Thr Cys Arg Arg Gly Val Pro
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic

<400> SEQUENCE: 39

Leu Tyr Arg Gly Gly Gln Arg Cys Arg Cys Val Cys Leu Arg Phe
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic

<400> SEQUENCE: 40

His Ser Gly Ala Thr Thr Thr Val Pro Ser Leu Ser Gly Lys Gly
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic

<400> SEQUENCE: 41

Met Ala Thr Gln Asp Ile Asp Gly Gln Tyr Ala Met Thr Arg Ala
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic

<400> SEQUENCE: 42

His Asn Gly Leu Ser Leu Gly Pro His Met Ser Ser Glu Leu Thr
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic

<400> SEQUENCE: 43

Ser Gln Pro Asn Ser Ser Asn Asn Ile Gln Ser Ile Thr Ser
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic

<400> SEQUENCE: 44

```
Ser Pro Ser Met Thr Glu Arg Asn Pro Leu Ser Gln Gln Glu Arg
1               5                   10                  15
```

<210> SEQ ID NO 45
<211> LENGTH: 15
<212> TYPE: PRT
<213> ORGANISM: Artificial Sequence
<220> FEATURE:
<223> OTHER INFORMATION: Synthetic

<400> SEQUENCE: 45

```
Glu Pro His Leu Pro Asn Pro Gly Asp Leu Ser Asn Thr Ile Ser
1               5                   10                  15
```

<210> SEQ ID NO 46
<211> LENGTH: 15
<212> TYPE: PRT
<213> ORGANISM: Artificial Sequence
<220> FEATURE:
<223> OTHER INFORMATION: Synthetic

<400> SEQUENCE: 46

```
Lys Ile Pro Val Ala Ile Lys Ala Pro Lys Ala Asn Lys Glu Ile
1               5                   10                  15
```

<210> SEQ ID NO 47
<211> LENGTH: 15
<212> TYPE: PRT
<213> ORGANISM: Artificial Sequence
<220> FEATURE:
<223> OTHER INFORMATION: Synthetic

<400> SEQUENCE: 47

```
Ile Pro Val Ala Ile Lys Glu Ser Pro Lys Ala Asn Lys Glu Ile
1               5                   10                  15
```

<210> SEQ ID NO 48
<211> LENGTH: 15
<212> TYPE: PRT
<213> ORGANISM: Artificial Sequence
<220> FEATURE:
<223> OTHER INFORMATION: Synthetic

<400> SEQUENCE: 48

```
Lys Ile Pro Val Ala Ile Lys Asp Pro Lys Ala Asn Lys Glu Ile
1               5                   10                  15
```

<210> SEQ ID NO 49
<211> LENGTH: 15
<212> TYPE: PRT
<213> ORGANISM: Artificial Sequence
<220> FEATURE:
<223> OTHER INFORMATION: Synthetic

<400> SEQUENCE: 49

```
Ile Pro Val Ala Ile Lys Glu Pro Lys Ala Asn Lys Glu Ile Leu
1               5                   10                  15
```

<210> SEQ ID NO 50
<211> LENGTH: 15
<212> TYPE: PRT
<213> ORGANISM: Artificial Sequence
<220> FEATURE:
<223> OTHER INFORMATION: Synthetic

<400> SEQUENCE: 50

```
Ile Pro Val Ala Ile Lys Glu Ser Lys Ala Asn Lys Glu Ile Leu
```

<210> SEQ ID NO 51
<211> LENGTH: 15
<212> TYPE: PRT
<213> ORGANISM: Artificial Sequence
<220> FEATURE:
<223> OTHER INFORMATION: Synthetic

<400> SEQUENCE: 51

Ala Leu Leu Arg Ile Leu Lys Lys Thr Glu Phe Lys Lys Ile Lys
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic

<400> SEQUENCE: 52

Ser Ser Val Ala Leu Asp Gln Arg Glu Glu Val Pro Leu Thr Thr
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic

<400> SEQUENCE: 53

Gln Gln Gln Gln Gln Gln Gln Leu Asp Leu Leu Phe His Gln Arg
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic

<400> SEQUENCE: 54

Lys Leu Arg Thr Asn Arg Glu Val Cys Phe Glu Ser Glu Ser Glu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic

<400> SEQUENCE: 55

His Gly His Phe Gln Pro Thr Glu Thr Gly Phe Leu Gln Pro Gly
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic

<400> SEQUENCE: 56

Glu Lys Glu Lys Ala Glu Glu Thr Gly Arg Gly Gly Ala Gly Arg
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic

<400> SEQUENCE: 57

Gly Gly Ala Gly Arg Gly Gly Pro Pro Gly Glu Gly Gly Gly
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic

<400> SEQUENCE: 58

Ile Thr Glu Gly Gly Glu Arg Arg Gly Gln Gly Ala Arg Gly Gly
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic

<400> SEQUENCE: 59

Gly Ala Arg Gly Gly Ser Gly Leu Gly Gly Gly Ala Lys Val Trp
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic

<400> SEQUENCE: 60

Arg Gly Gly Ser Gly Leu Gly Gly Gly Ala Lys Val Trp Leu Leu
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic

<400> SEQUENCE: 61

Val Gly Tyr Ser Leu Glu Ile Glu Thr Ala Leu Thr Ser Gln Ser
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic

<400> SEQUENCE: 62

Val Leu Gly Pro Glu His Thr Asp Leu Gln Gly Pro Gly Thr Asp
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic

<400> SEQUENCE: 63

Lys Asp Ile Leu Glu Gln Ala Gly Pro Arg Trp Thr Pro Thr Ala
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic

<400> SEQUENCE: 64

Gln Lys Asp Ile Leu Glu Gln Glu Arg Gly Pro Arg Trp Thr Pro
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic

<400> SEQUENCE: 65

Ala Tyr Ser Ala His Ser Ala His Ser Ala Pro Thr Ser Phe Pro
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic

<400> SEQUENCE: 66

Val Pro Arg Trp Ser Asn Ala Asn Met Glu Ile Ala Thr Lys Asp
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic

<400> SEQUENCE: 67

Ala Trp Pro Glu Glu Trp Gly Gly Gln Ala His Arg Gln Arg Asn
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Synthetic

<400> SEQUENCE: 68

Pro Glu Glu Trp Gly Gly Ala Arg Arg Thr Gly Arg Gly Thr Ser
1               5                   10                  15

```
<210> SEQ ID NO 69
<211> LENGTH: 15
<212> TYPE: PRT
<213> ORGANISM: Artificial Sequence
<220> FEATURE:
<223> OTHER INFORMATION: Synthetic

<400> SEQUENCE: 69

Thr Gly Glu Gln Arg Thr Glu Glu Leu Thr Glu Ala Glu Leu Leu
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic

<400> SEQUENCE: 70

Leu Leu Asp Ile Leu Asp Thr Thr Gly Gln Glu Glu Tyr Ser Ala
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Synthetic

<400> SEQUENCE: 71

Asn Gln Ser Leu Leu Gln Pro Val Asn Val Glu Ile Asp Pro Gln
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Synthetic

<400> SEQUENCE: 72

Tyr Pro Thr Leu Gly Leu Pro Glu Asp Met Met Val Met Leu Pro
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic

<400> SEQUENCE: 73

Met Gly Val Leu Gly Pro Leu Thr Ile Asp Pro Asn Met Leu Asn
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic

<400> SEQUENCE: 74

Arg Cys Phe Pro Val Ile Phe Asp Lys Ala Ser Glu Ser Leu Lys
1               5                   10                  15

<210> SEQ ID NO 75
```

```
<211> LENGTH: 15
<212> TYPE: PRT
<213> ORGANISM: Artificial Sequence
<220> FEATURE:
<223> OTHER INFORMATION: Synthetic

<400> SEQUENCE: 75

Pro Phe Phe Phe Tyr Pro Ile Cys Thr Ser Trp His Cys Asn Arg
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic

<400> SEQUENCE: 76

Ser Met Pro Ala Ser Pro Pro Arg Ser Glu Ala Pro Ser Thr Cys
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic

<400> SEQUENCE: 77

Ala Val Ser Gly Pro Pro Arg Glu Ala Ser Trp Asp Cys Arg Trp
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic

<400> SEQUENCE: 78

Tyr Ser Gln Ala Ser Ser Ser Pro Thr Thr Ala Asp Gly Thr Ser
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic

<400> SEQUENCE: 79

Lys Thr Gln Val Thr Ala Ser Ala Glu Ala Ser Ser Ser Thr Thr
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic

<400> SEQUENCE: 80

Ser Thr Pro Val Thr Thr Ser Ala Glu Ala Thr Ser Ser Pro Thr
1               5                   10                  15

<210> SEQ ID NO 81
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 81

Ser Ile Pro Val Thr Thr Ser Ala Glu Ala Ser Ser Ser Pro Thr
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic

<400> SEQUENCE: 82

Asn Thr Pro Val Thr Thr Ser Ala Glu Ala Thr Ser Ser Ser Thr
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic

<400> SEQUENCE: 83

Ser Thr Pro Val Thr Thr Ser Ala Glu Ala Ser Ser Ser Pro Thr
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic

<400> SEQUENCE: 84

Ser Thr Pro Val Thr Thr Ser Ala Glu Ala Thr Ser Ser Pro Thr
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic

<400> SEQUENCE: 85

Asn Thr Pro Val Thr Thr Ser Ala Glu Ala Thr Ser Ser Ser Thr
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic

<400> SEQUENCE: 86

Ser Thr Pro Val Thr Thr Ser Ala Glu Ala Thr Ser Ser Pro Thr
1               5                   10                  15

<210> SEQ ID NO 87
<211> LENGTH: 15
<212> TYPE: PRT
```

<213> ORGANISM: Artificial Sequence
<220> FEATURE:
<223> OTHER INFORMATION: Synthetic

<400> SEQUENCE: 87

Met Ala Gly Ser Glu Thr Thr Thr Val Ser Thr Ala Gly Ser Glu
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic

<400> SEQUENCE: 88

Gly Asp Phe His Asn His Asp Pro Ile Phe Ser Glu Tyr Arg His
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic

<400> SEQUENCE: 89

Tyr Arg Phe Pro Asp Tyr Ser Asn Arg Pro His Ile Asn Ile His
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic

<400> SEQUENCE: 90

His Pro Tyr Pro Cys Thr Asp Gly His Phe Cys Leu His Pro Leu
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic

<400> SEQUENCE: 91

Cys Leu His Pro Leu Asn Ala Asn Arg His Asp Ser Ser Thr Asp
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic

<400> SEQUENCE: 92

Ser Lys Gln Ser Thr Ala Ser Lys Gln Ser Thr Ala Ser Arg Gln
1               5                   10                  15

<210> SEQ ID NO 93
<211> LENGTH: 15
<212> TYPE: PRT
<213> ORGANISM: Artificial Sequence

```
<220> FEATURE:
<223> OTHER INFORMATION: Synthetic

<400> SEQUENCE: 93

Ala Ser Pro Ser Lys Leu Ser Asn Glu Glu Leu Ile Gln Ser Met
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic

<400> SEQUENCE: 94

Gln Gln Gln Gln Gln Gln Pro Asp Met Pro Arg Ser Ser Gln Glu
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic

<400> SEQUENCE: 95

Gln Gln Gln Gln Gln Gln Pro Asp Asp Asp Met Pro Arg Ser
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Synthetic

<400> SEQUENCE: 96

Leu Glu Pro Gly Leu Asp Glu Lys Asp Thr Asp Phe Glu Glu Glu
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Synthetic

<400> SEQUENCE: 97

Ala Gln Leu Gln Leu Asp Glu Lys Thr Gly Glu Phe Leu Pro Ile
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic

<400> SEQUENCE: 98

Glu Lys Arg Lys Lys Arg Arg Gly Leu Phe Ser Lys Ala Gln Thr
1               5                   10                  15

<210> SEQ ID NO 99
<211> LENGTH: 15
<212> TYPE: PRT
<213> ORGANISM: Artificial Sequence
<220> FEATURE:
```

```
<223> OTHER INFORMATION: Synthetic

<400> SEQUENCE: 99

Asp Gln Glu Ala Ile Gln Asp Leu Trp Ser Ala Val Glu Glu Val
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthetic

<400> SEQUENCE: 100

Glu Asp Ala Asp Glu Asn Ile Asn Val Thr Ser Asn Asp Pro Glu
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic

<400> SEQUENCE: 101

Val His Phe His Asp Asn Ser Glu Asp Val Phe His Ala His Ser
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic

<400> SEQUENCE: 102

Gly Ser Ala Gly His Gly Thr Gly Phe His Ser His Cys His Phe
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic

<400> SEQUENCE: 103

Ile Lys Gly Thr Ala Gly Gly Ser Asp Pro Thr Ile Glu Leu Ser
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic

<400> SEQUENCE: 104

Glu Lys Thr Cys Lys Glu Cys Met Pro Glu Phe Phe Leu His Asp
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Synthetic
```

<400> SEQUENCE: 105

Ala Leu Met Glu Glu Phe Phe Pro Gln Gly Asp Lys Glu Ala Glu
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Synthetic

<400> SEQUENCE: 106

Ala Ala Glu Tyr Arg Glu Ile Gly Lys Arg Met Asn Ser Ile Lys
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Synthetic

<400> SEQUENCE: 107

Thr Leu Thr Leu Arg Lys Gly Arg Asn Asn Lys Leu Ile Lys Ile
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic

<400> SEQUENCE: 108

Ser Val Leu Thr Glu Val Glu Pro Gln Thr Ile Glu Glu Leu Lys
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Synthetic

<400> SEQUENCE: 109

Pro Pro Ser Pro Ala Pro Ala His Phe Thr Ala Arg Gly Gly Arg
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthetic

<400> SEQUENCE: 110

Thr Ser Ser Ala Phe Val Gly Asn Thr Pro Glu Ala Ser Pro Glu
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Synthetic

```
<400> SEQUENCE: 111

Leu Arg Gly Ser Ile Val Gly Glu His Glu Pro Gly Glu Pro Arg
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Synthetic

<400> SEQUENCE: 112

Gly Pro Pro Arg Ser Ala Pro Arg Gly Cys Leu His Val Gly Arg
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthetic

<400> SEQUENCE: 113

Gln Ala Arg His Thr Gly Ile Glu Ile Val Gln Gln Ile Ala Ile
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic

<400> SEQUENCE: 114

Lys Gln Gln Gln Gln Gln Gln Gln Gln Gln Lys Gln Gln Gln Glu
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic

<400> SEQUENCE: 115

Arg Thr Arg Gly Ser Pro Leu Arg Leu Thr Leu Trp Pro Pro Arg
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic

<400> SEQUENCE: 116

Asp Leu Cys Pro Leu Lys Asn Gln Val Asp Ser Ser Leu Pro Ala
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic

<400> SEQUENCE: 117
```

Ala Ala Ala Gly Ile Gly Val His Asp Leu Arg Arg Leu Cys Ile
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Synthetic

<400> SEQUENCE: 118

Gln Thr Arg Gln Asn Gly Ile His Thr Asn Lys Pro Ala Leu Arg
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Synthetic

<400> SEQUENCE: 119

Cys Val Glu Arg Cys Pro Trp Lys Gly Ile Cys Trp Lys Trp Pro
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Synthetic

<400> SEQUENCE: 120

Glu Asn Asp Pro Gly Asp Ser Asn Tyr Thr Val Asp Leu Leu Asp
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Synthetic

<400> SEQUENCE: 121

Asn Thr Lys Tyr Thr Phe Lys Thr Val Ser Pro Asn Lys Pro
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Synthetic

<400> SEQUENCE: 122

Ile Glu Ala Leu Thr Lys Lys Arg Glu Ser Thr Leu Gly Asn Phe
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Synthetic

<400> SEQUENCE: 123

-continued

```
Ser Thr Pro Pro Pro Gly Thr Ala Ser Ala Pro Trp Pro Ser Thr
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Synthetic

<400> SEQUENCE: 124

His Pro Arg Pro Ala Pro Ala Ser Ala Pro Trp Pro Ser Thr Ser
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Synthetic

<400> SEQUENCE: 125

Met Ser Ala Ala Gln Ile Ala Met Val Trp Pro Leu Leu Ser Ile
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Synthetic

<400> SEQUENCE: 126

Thr Ser Cys Pro Gln Gly Ala Leu Ser Glu His Cys Pro Thr Thr
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Synthetic

<400> SEQUENCE: 127

Ser Glu His Cys Pro Thr Thr Pro Ala Pro Leu Pro Ser Gln Arg
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Synthetic

<400> SEQUENCE: 128

Arg Arg Pro Ile Leu Thr Ile Phe Thr Leu Glu Asp Ser Ser Gly
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Synthetic

<400> SEQUENCE: 129

Arg Arg Pro Ile Leu Thr Ile Asn Thr Leu Glu Asp Ser Ser Gly
```

```
<210> SEQ ID NO 130
<211> LENGTH: 15
<212> TYPE: PRT
<213> ORGANISM: Artificial Sequence
<220> FEATURE:
<223> OTHER INFORMATION: Synthetic

<400> SEQUENCE: 130

Thr Tyr Ser Pro Ala Leu Asn Glu Met Phe Cys Gln Leu Ala Lys
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Synthetic

<400> SEQUENCE: 131

Gly Met Asn Arg Arg Pro Ile Pro Thr Ile Ile Thr Leu Glu Asp
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Synthetic

<400> SEQUENCE: 132

Ala Pro Pro Gln His Leu Ile Pro Val Glu Gly Asn Leu Arg Val
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Synthetic

<400> SEQUENCE: 133

Cys Met Gly Gly Met Asn Arg Met Pro Ile Leu Thr Ile Ile Thr
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Synthetic

<400> SEQUENCE: 134

Ala Cys Pro Gly Arg Asp Arg Pro Thr Glu Glu Glu Asn Leu Arg
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Synthetic

<400> SEQUENCE: 135

Arg Glu Arg Phe Glu Met Phe Pro Glu Leu Asn Glu Ala Leu Glu
1               5                   10                  15
```

<210> SEQ ID NO 136
<211> LENGTH: 15
<212> TYPE: PRT
<213> ORGANISM: Artificial Sequence
<220> FEATURE:
<223> OTHER INFORMATION: Synthetic

<400> SEQUENCE: 136

Arg His Ser Val Val Val Pro Asn Glu Pro Pro Glu Val Gly Ser
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Synthetic

<400> SEQUENCE: 137

His Leu Ile Arg Val Glu Gly Ile Cys Val Trp Ser Ile Trp Met
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Synthetic

<400> SEQUENCE: 138

Gly Gly Met Asn Arg Arg Pro Ser Ser Pro Ser Ser His Trp Lys
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Synthetic

<400> SEQUENCE: 139

Ser Gln Arg Arg Asn His Trp Met Glu Asn Ile Ser Pro Phe Arg
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Synthetic

<400> SEQUENCE: 140

Ala Pro Leu Pro Ser Gln Arg Arg Asn His Trp Met Glu Asn Ile
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Synthetic

<400> SEQUENCE: 141

Ala Asp Gly Ala His Pro Pro Ala Thr Pro Leu Arg Gly Ala Glu
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Synthetic

<400> SEQUENCE: 142

Lys Pro Ser Arg Lys Val Asp Asp Ser Leu Thr Ile Asp Thr Ala
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Synthetic

<400> SEQUENCE: 143

Pro Pro Gln Glu Ala Asp Ala Lys Arg Gln Arg Gln Trp Gln Trp
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: Synthetic

<400> SEQUENCE: 144

Arg Arg Lys Glu Arg Pro Ala Arg Thr Pro Pro Gly Gly Gly Arg
1               5                   10                  15

<210> SEQ ID NO 145
<211> LENGTH: 15
<212> TYPE: PRT
<213> ORGANISM: Artificial Sequence
<220> FEATURE:
<223> OTHER INFORMATION: Synthetic

<400> SEQUENCE: 145

Ser Ala Cys Cys Ala Pro Arg Pro Thr His Ser Ser Ala Thr Gln
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: Synthetic

<400> SEQUENCE: 146

Ala Thr Leu Pro Cys Arg Arg His Cys Pro Arg Cys Pro Ala Pro
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Synthetic

<400> SEQUENCE: 147

Val Ala Phe Leu Pro Pro Met His Cys Pro Thr Ala Thr Ala Ala
1               5                   10                  15

```
<210> SEQ ID NO 148
<211> LENGTH: 15
<212> TYPE: PRT
<213> ORGANISM: Artificial Sequence
<220> FEATURE:
<223> OTHER INFORMATION: Synthetic

<400> SEQUENCE: 148

Ser Pro Glu Glu Thr Ser Thr Glu Arg Ser Ile Lys Gln Asn Ser
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Synthetic

<400> SEQUENCE: 149

Phe Gly Lys Ile Phe Asn Ser Cys Ile Asn Ile Val His Val Gly
1               5                   10                  15
```